(12) United States Patent
Taguchi

(10) Patent No.: US 6,907,100 B2
(45) Date of Patent: Jun. 14, 2005

(54) CONE BEAM TYPE OF X-RAY CT SYSTEM FOR THREE-DIMENSIONAL RECONSTRUCTION

(75) Inventor: Katsuyuki Taguchi, Buffalo Grove, IL (US)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/278,872

(22) Filed: Oct. 24, 2002

(65) Prior Publication Data

US 2004/0086074 A1 May 6, 2004

(30) Foreign Application Priority Data

Oct. 25, 2001 (JP) .................................. P2001-327789
Oct. 16, 2002 (JP) .................................. P2002-301432

(51) Int. Cl.[7] .............................................. A61B 6/03
(52) U.S. Cl. ............................ 378/4; 378/19; 378/901
(58) Field of Search ........................... 378/4, 8, 15, 19, 378/901

(56) References Cited

U.S. PATENT DOCUMENTS

| | | | |
|---|---|---|---|
| 5,706,325 A | 1/1998 | Hu | |
| 5,784,481 A | 7/1998 | Hu | |
| 5,960,055 A | * 9/1999 | Samarasekera et al. | 378/4 |
| 5,970,111 A | * 10/1999 | Samarasekera et al. | 378/4 |
| 6,009,142 A | * 12/1999 | Sauer et al. | 378/15 |
| 6,014,419 A | 1/2000 | Hu | |
| 6,542,570 B1 | 4/2003 | Silver | |
| 6,546,067 B2 | 4/2003 | Aradate et al. | |
| 6,560,308 B1 | 5/2003 | Zmora | |
| 6,574,297 B2 | * 6/2003 | Tam | 378/15 |
| 6,584,166 B2 | 6/2003 | Taguchi | |

* cited by examiner

Primary Examiner—David V Bruce
(74) Attorney, Agent, or Firm—Oblon, Spivak, McClelland, Maier & Neustadt, P.C.

(57) ABSTRACT

An X-ray CT system is equipped with a gantry, couch and control cabinet and configured to scan a cone-beam X-ray toward an object along a given orbit to acquire cone-beam data in which a three-dimensional distribution of an X-ray absorption coefficient within the object is reflected. The control cabinet decides a degree of reliability for the cone-beam data according to an acquisition time of the cone-beam data, and then decides a weight for three-dimensional Radon data from the cone-beam data on the basis of the degree of reliability. Using this weight, the control cabinet reconstructs the three-dimensional Radon data based on a three-dimensional reconstruction algorithm. Thus, when the three-dimensional reconstruction algorithm for cone-beam CT is applied to medical CT, artifacts attributable to object's motion can be suppressed and temporal resolution can be improved.

25 Claims, 30 Drawing Sheets

(2D-RADON DATA AT EACH POINT
INSIDE CIRCLE OF RADIUS r IS
ACQUIRED TWO TIMES.)

(TEMPORARY SENSITIVITY PROFILE OF FS)

(2D-RADON DATA INSIDE CIRCLE OF RADIUS r IS ACQUIRED AT LEAST ONE TIME WITHIN $\beta = [0, \pi + 2\gamma m]$.)

(TEMPORARY SENSITIVITY PROFILE OF HS)

(TEMPORARY SENSITIVITY PROFILE OF US)

(3D-RADON DATA($\xi$, $\phi$, s) IS ACQUIRED ON LINE L AT FOCAL POINT $\beta$.)

( 3D-RADON DATA ACQUIRABLE AT FOCAL POINT $\beta=0$ )

(TO RECONSTRUCT OBJECT f SUPPORTED BY SPHERE OF RADIUS r, 3D-RADON DATA IS REQUIRED WITHIN SPHERE OF RADIUS r.)

(3D-RADON DATA ACQUIRED BY SCANNING ALONG CIRCULAR
ORBIT OF RADIUS R ABOUT z-AXIS AT z=0 PLANE)

(VIEW PRODUCED BY OVERLAPPING VIEW SHOWN IN FIG. 23 ON
VIEW SHOWN IN FIG. 24)

(3D-RADON DATA ACQUIRABLE BY SCANNING ALONG CIRCULAR ORBIT OF
RADIUS R BY AMOUNT OF $\beta = [0, \pi + 2\gamma m]$ ABOUT z-AXIS AT z=0 PLANE.
THE DATA IN THE VICINITY OF $\beta = 0$ AND $\pi + 2\gamma m$ IS CONVERGED TO
ZERO DUE TO WEIGHTING.)

(VIEW PRODUCED BY OVERLAPPING VIEW SHOWN IN FIG. 23
ON VIEW SHOWN IN FIG. 26)

[EXAMPLE OF DATA RELIABILITY FUNCTION DURING A CIRCULAR-OBIT SCAN CONSISTING OF A PLURALITY OF TIMES OF CONTINUOUS ROTATIONS]

[EXAMPLE OF DATA RELIABILITY FUNCTION DURING A HELICAL SCAN]

(VIEW ALONG A-DIRECTION)

(VIEW ALONG A-DIRECTION)

(VIEW ALONG A-DIRECTION)

CONE BEAM TYPE OF X-RAY CT SYSTEM FOR THREE-DIMENSIONAL RECONSTRUCTION

BACKGROUND OF THE INVENTION

1. Technical Field of the Invention

The present invention relates to an X-ray CT system for performing a scan using an cone-like X-ray beam, and in particular, to an X-ray CT system, which is also called cone-beam CT system, that is able to acquire two-dimensional projection data of transmitted X-rays using a two-dimensional detector and obtain CT images by applying three-dimensional reconstruction to the two-dimensional projection data.

2. Related Art

An X-ray CT scanner is provided a gantry in which both of an X-ray tube (X-ray radiation device) and an X-ray detector are disposed to make an object locate therebetween. For example, when an R-R driving technique is adopted, both the X-ray tube and the X-ray detector are driven in synchronism with each other to be rotated about the object, and X-ray beams radiated from the X-ray tube are made to enter the X-ray detector through the object. A DAS (data acquisition system) is connected to the X-ray detector, so that data indicative of intensity of projected X-rays is acquired by the DAS for every scan. Reconstructing the acquired projection data produces internal image data of the object (i.e., slice data or volume data).

In the field of such an X-ray CT scanner, in recent years, CT that involves scanning based on a cone beam, that is, cone-beam CT has been studied eagerly, as one approach to fast producing three-dimensional images of higher resolution.

For example, a Japanese Patent Laid-open publication No. HEI 9-19425 proposes an X-ray computer tomography imaging system serves as a cone-beam CT scanner, wherein error in reconstruction, which is attributable to shifts between an actually-measured X-ray path and a computed X-ray path, is relieved to improve image quality.

In addition, another Japanese Patent Laid-open publication No. 2000-102532 proposes an X-ray CT scanner serving as a cone-beam CT scanner, which is able to accurately acquire projection data of high resolution by performing a scan using a cone beam produced from continuous X-rays. This acquisition is achieved, with the circuitry of DAS kept to a practical size, without prolonging a scan time, and with a less effective path even when shifts occur in acquisition timing of projection data.

However, if the above-listed conventional cone-beam CT scanners are desired to be used as an actual CT scanner, such CT scanners will encounter problems resulted from the fact that an object, that is, a patient may move during a scan. That is, when a universal three-dimensional reconstruction algorithm is applied to projection data to obtain images, without taking the object motion into consideration, artifacts arise on the images and temporal resolution deteriorates.

SUMMARY OF THE INVENTION

An object of the present invention is to provide, with due consideration to the drawbacks of the above conventional configurations, an X-ray system and a three-dimensional reconstruction method for cone-beam CT, which are capable of reducing artifacts resulting from movements of an object when a three-dimensional reconstruction algorithm for cone-beam CT is applied to medical CT and improving temporal resolution.

In order to achieve the above object, an X-ray CT system according to the present invention comprises, basically, an X-ray source for radiating a cone-beam X-ray; a two-dimensional X-ray detector for detecting the X-ray radiated from the X-ray source and made to transmit an object to be examined and for outputting projection data depeding on an amount of the X-ray; scanning means configured to scan the object with the X-ray radiated from the X-ray source within a particular scan range under a desired scan technique involving at least a movement of the X-ray source along a predetermined orbit thereof, thus making the X-ray detector to acquire the projection data generated by the scan; Radon data producing means for producing three-dimensional Radon data distributed three-dimensionally, from the projection data through the scanning means; weighting means for weighting the three-dimensional Radon data based on a weighting function providing a non-constant weight with regard to an acquisition time of the projection data; and reconstruction means for reconstructing the three-dimensional Radon data weighted by the weighting means, based on a desired three-dimensional reconstruction algorithm, so that an image is obtained by the reconstruction.

Preferably, the weighting means is configured to perform the weighting correspondingly to each plane to be subjected to surface integral for obtaining individually the three-dimensional Radon data.

By way of example, the weighting means is configured to weight the three-dimensional Radon data produced from the projection data acquired in the scan range by using, as the weighting function, a weighting function giving not only a maximum weight at a data acquisition time representative of a time of the image reconstructed by the reconstruction means but also a smaller weight at another data acquisition time different from the data acquisition time representing the maximum weight.

Further, by way of example, the weighting means may be configured to weight the three-dimensional Radon data produced from the projection data acquired in the scan range by using, as the weighting function, a weighting function giving not only a maximum weight at both a data acquisition time representative of a time of the image reconstructed by the reconstruction means and another data acquisition time falling in a smaller temporal range including the data acquisition time representing the maximum weight but also giving a smaller weight at another data acquisition time different from the data acquisition time representing the maximum weight.

Still further, by way of example, the weighting means may be configured to weight the three-dimensional Radon data produced from the projection data acquired in the scan range by using, as the weighting function, a weighting function giving not only a maximum weight at a data acquisition time representative of a time of the image reconstructed by the reconstruction means but also a weight becoming smaller as going away from the data acquisition time representing the maximum weight.

It is preferred that the weighting function is set according to a type of the scan technique. This scan technique consists of, for example, a scan technique based on a circular-orbit full scan representing as the orbit a one-time circular orbit, a circular-orbit half scan (MHS: Modified Half Scan) along an extended circle using the projection data from the scan range of 360 degrees while the orbit representing a one-time circular orbit, a circular-orbit under scan representing as the orbit a one-time circular orbit, a circular-orbit scan representing as the orbit two or more rotations along a circular orbit, a scan representing as the orbit an orbit formed by combining a linear orbit and a circular orbit, or a helical scan representing as the orbit a helical orbit.

Meanwhile, in order to achieve the foregoing object, the present invention provides a three-dimensional reconstruction method comprises the steps of: acquiring two-dimensional projection data into which a three-dimensional distribution of an X-ray absorption coefficient of an object to be examined is reflected, by scanning the object with a cone-beam X-ray; producing three-dimensional Radon data from the projection data; correcting the three-dimensional Radon data based on a weighting function in which a degree of reliability of the projection data is reflected, the degree of reliability being previously decided depending on an acquisition time of the projection data; and allowing the three-dimensional Radon data to be subject to a three-dimensional reconstruction algorithm to reconstruct the three-dimensional Radon data of the object. By way of example, the correcting step is configured to correct the three-dimensional Radon data by using the weighting function, correspondingly to each plane to be subjected to surface integral for obtaining individually the three-dimensional Radon data.

Still, in the present invention, in order to achieve the foregoing object, there is provided a weight setting method for X-ray CT comprising the steps of: deciding a degree of reliability for two-dimensional projection data on the basis of a acquisition time of the two-dimensional projection data in which a three-dimensional distribution of an X-ray absorption coefficient of an object to be examined is reflected, the three-dimensional distribution being acquired with a cone-beam X-ray; deciding a weight used to correct a three-dimensional Radon data obtained from the projection data on the basis of the degree of reliability.

Accordingly, for applying the cone-beam-CT three-dimensional reconstruction algorithm to medical CT imaging, even when an object to be imaged moves during a scan, artifacts due to object's motion can be reduced without failure, while still improving temporal resolution.

Practical configurations and features according to the other modes of the present invention will be clearly understood from the following description of embodiments and appended drawings.

DETAILED EXPLANATION OF PREFERRED EMBODIMENTS

Referring to FIGS. 1 to 37, an X-ray CT system according to the present invention will now be described. A three-dimensional reconstruction algorithm for X-ray CT and a method of setting a correction function for the X-ray CT according to the present invention will now be described in the explanation of the X-ray CT system, because they are practiced together with the functions of the X-ray CT system.

Figure 1:
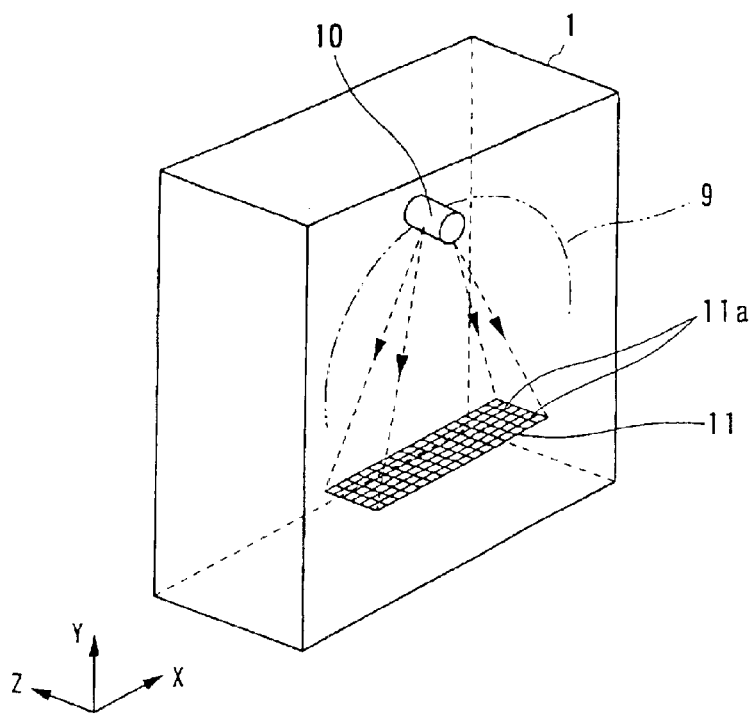
FIG. 1 explains the positional relationship between an X-ray tube and a two-dimensional detector in a gantry of an X-ray CT scanner (X-ray system) according to an embodiment of the present invention.
Figure 2:
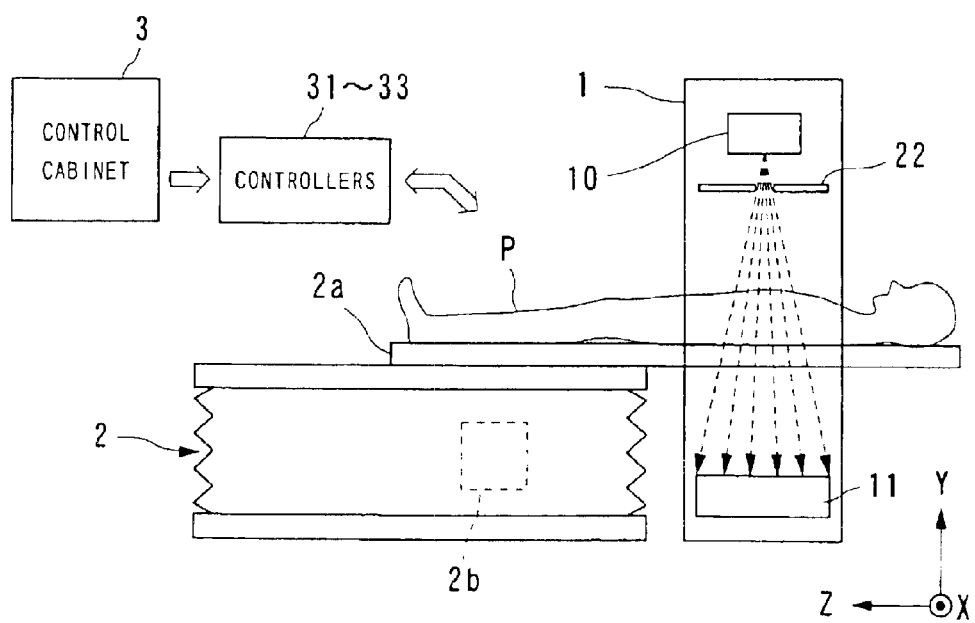
FIG. 2 outlines the configuration of the X-ray CT scanner.
Figure 3:
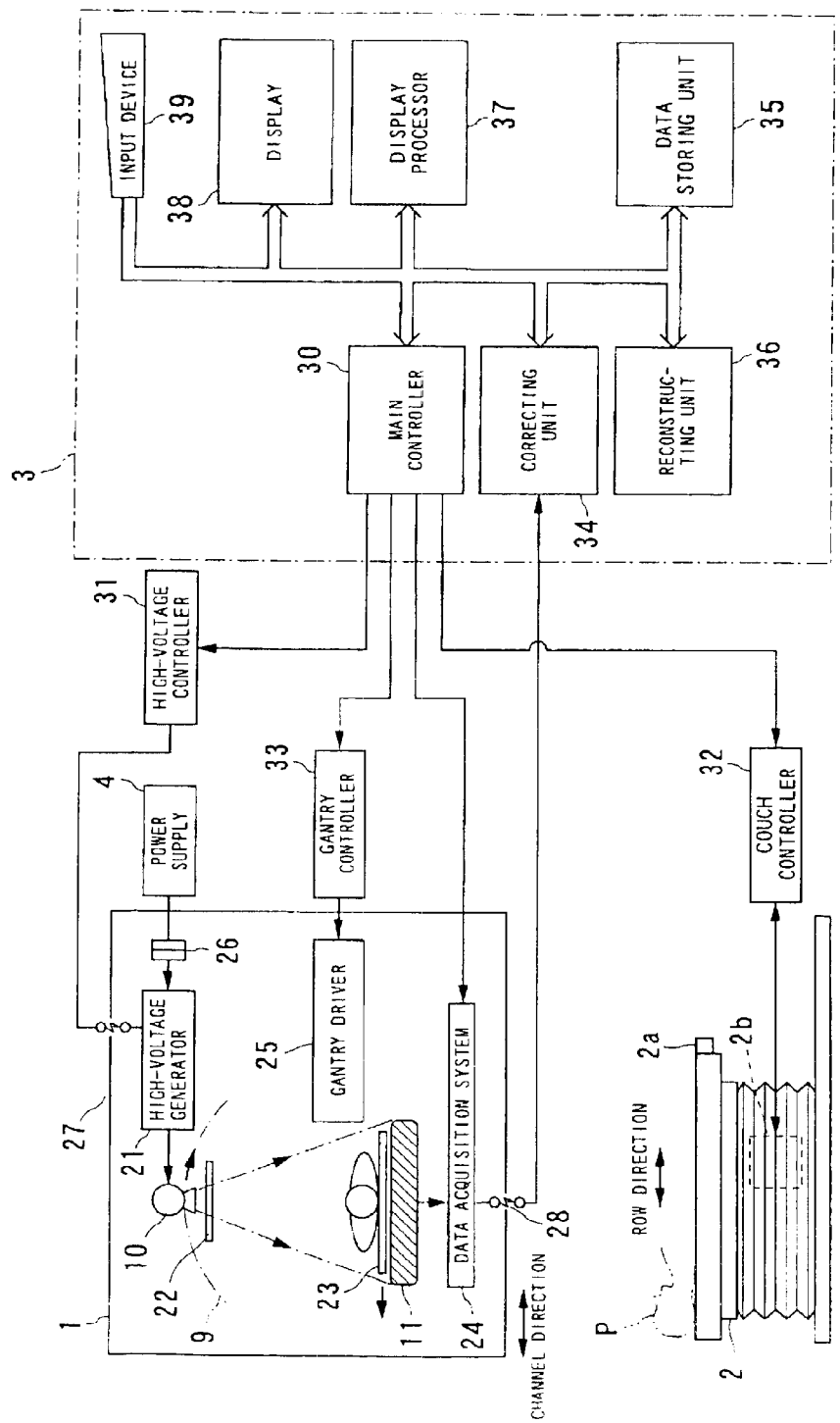
FIG. 3 is an outlined block diagram showing an electrical system incorporated in the X-ray CT scanner.

An X-ray CT scanner (i.e., X-ray CT system) shown in FIGS. 1 to 3 is provided with a gantry 1, a couch 2, a control cabinet 3, a power supply 4, and various controllers and is driven, for example, in an R-R drive manner. The various types of controllers include a high-voltage controller 31, a gantry controller 33, and a couch controller 32.

As shown in FIGS. 1 and 2, the longitudinal direction of the couch 2 is designated as a low direction Z (or rotation-axis direction or slice direction) and the two directions orthogonal to this direction Z are defined as a channel direction X and a beam radiating direction Y, respectively.

On the top of the couch 2, a couch top 2a is disposed so that the couch top is slidable along the longitudinal direction (row direction Z). An object P to be examined is laid on the couch top 2a. The couch top 2a is driven by a couch driver 2b, which is represented by a servo motor, such that the couch top can be inserted in a retractable manner into a diagnostic opening (not shown) of the gantry 1. A drive signal is supplied from a couch controller 32 to the couch driver 2b. The couch 2 is also provided with a position detector (not shown) formed by components including an encoder to detect a position of the couch top 2a in the couch-longitudinal direction in the form of an electrical signal and the detected signal is sent to the couch controller 32 as a signal for controlling the couch.

In the gantry 1, as shown in FIGS. 1 and 3, there is provided an approximately cylindrical rotation frame 9. The foregoing diagnostic opening is located to pass through the rotation frame 9. On the rotation frame, both an X-ray tube 10 and a two-dimensional detector 11 serving as an X-ray detector are disposed so that they are opposed to each other with an object P therebetween, the object being inserted into the diagnostic opening located through the rotation frame 9. In addition, as pictorially shown in FIG. 9, at predetermined positions on the rotation frame 9, there are arranged a high-voltage generator 21, a pre-collimator 22, a scattered-ray removing collimator 23 functioning as a post-collimator, a data acquisition system (DAS) 24, and a gantry driver 25.

Of these components, the X-ray tube 10, which serves as an X-ray source, is structured into for example a rotating anode tube and responds to continuous supply of current to a filament thereof from the high-voltage generator 21 causes the filament to be heated, thus thermal electrons being radiated to a target thereof. Impinging the thermal electrons onto the target surface forms an effective focal point thereon, resulting in that an X-ray beam is continuously radiated, with a spread, from a portion of the effective focal point on the target surface.

To the high-voltage generator 21 are supplied a low-voltage power from the power supply 4 via a low-voltage slip ring 26 and a control signal for X-ray radiation from the high-voltage generator 21 through an optical-signal transmission system 27. Thus the high-voltage generator 21 produces a high-voltage power from the supplied low-voltage power and produces a continuous tube voltage from this high-voltage power in response to the control signal. The tube voltage is provided to the X-ray tube 10.

The pre-collimator 22 is located between the X-ray tube 10 and an object P, while the scattered-ray removing collimator 23 functioning as a post-collimator is located between the object P and the two-dimensional detector 11. The pre-collimator 22 forms, for example, a slit-like opening having a given width in the row direction Z. Thus the pre-collimator 22 limits a total width of an X-ray beam radiated from the X-ray tube 10 in the row direction Z, so that produced is, for example, a cone-shaped X-ray beam of a desired slice width that corresponds to the sum of desired plural detection element rows of the two-dimensional detector 11.

Under the rotation of the rotation frame 9, both of the X-ray tube 10 and the two-dimensional detector 11 also rotate, while they are kept to be opposed to each other, about a rotation center axis in the axial direction of the diagnostic opening.

As the two-dimensional detector 11, any of a flat type of detector shaped as a whole into a flat panel or a cylindrical type of detector shaped as a whole into a curved panel can be adopted. In the present embodiment, a flat type of detector will be exemplified. (In the present invention, a cylindrical type of detector can be adopted.) The two-dimensional detector 11 is formed into a detector, wherein a plurality of detection element rows each having plural detection channels are disposed in the slice direction (refer to FIG. 1). Each detection element has a detection part composed of, by way of example, a solid state detector of a scintillator and a photo detector, which converts an incident X-ray into an optical signal, and then to convert the optical signal to an electrical signal. Additionally, each detection element has electric-charge storage (sample hold). Thus, the two-dimensional detector 11 is structured such that selecting a group of switches of the DAS 24 in turn to read out electric charges from the electric charge storages will lead to detection of signals (i.e., projection data) indicative of intensities of transmission X-rays. Incidentally, each detection element may be formed by a sensor (such as an I.I.) capable of directly converting an incident X-ray into an electric signal.

The DAS 24 is structured into a filter DAS that responds to switchovers of a group of switches thereto to read out in sequence detection signals from the detection sensors and then to apply A/D conversion to the read detection signals (sampling in the form of voltage). To perform this, considering that the detector 11 is formed into a two-dimensional detector, the DAS 24 is provided with, for example, a row selector for N-channels, a single channel sector, a signal A/D converter, and a control circuit.

A data transmission system 28 is in charge of connecting signal paths on the rotation side of the gantry 1 and the stationary side, one example thereof is an optical transmission system that is a non-contact signal transmission. The data transmission system 28 may be formed by a slip ring. Digital-amount projection data read out through this data transmission system 28 is then sent to a correction unit installed in the control cabinet 3, as will be described later.

Further, the gantry driver 25 includes various components, such as motors and gear mechanisms, to rotate the entire rotary components, together with the rotation frame 9, about its center axis. The gantry driver 25 receives a drive signal from the gantry controller 33.

The high-voltage controller 31, couch controller 32, and gantry controller 33 are placed, in terms of signal transmission, between the gantry 1 and the couch 2 and the control cabinet 3 and configured to individually respond to a control signal coming from a main controller described later to drive each load element assigned to each controller.

The control cabinet 3 is equipped with a main controller 30 that controls the entire system and a correction unit. 34, data storing unit 35, reconstruction unit 36, display processor 37, display 38, and input device 39.

The correction unit 34 responds to a processing command from the main controller 30 such that various types of correction processing, such as offset correction and calibration, are applied to digital projection data transmitted from the DAS 24. The acquired and collected data is temporarily stored and preserved in the data storing unit 35 in response to a write command from the main controller 30. The stored data will be read out from the data storing unit 35 responsively to a read command issued at a desired timing from the main controller 30, and then transferred to the reconstruction unit 36.

The reconstruction unit 36, which operates under control of the main controller 30, performs reconstruction processing on the acquired data that has been transmitted for reconstruction. The reconstruction processing is based on a three-dimensional reconstruction algorithm to which a three-dimensional reconstruction technique (described later) for cone-beam CT according to the present invention is applied. Accordingly, the reconstruction unit 36 produces image data in a three-dimensional region through the three-dimensional reconstruction algorithm. Under the control of the main controller 30, the reconstructed image data is preserved, if necessary, in the data storing unit 35 and sent to the display processor 37.

The display processor 37 performs necessary processing, such as coloring processing and overlapping processing of annotation data and scan information, on the image data, thus resultant image data being sent to the display 38.

The display 38 is in charge of A/D conversion of the image data and visualization of the image data as a tomographic image.

The input device 39 is used for providing the main controller 30 with commands including scan conditions (such as a region and a position to be scanned, slice thickness, voltage and current for the X-ray tube, and a scanning direction in an object) and image display conditions.

Referring to FIGS. 4 to 27, the principle of a three-dimensional reconstruction algorithm for cone-beam CT, which is an essential issue in the present embodiment, will now be described.

In the following, from inventor's point of view, a known two-dimensional reconstruction algorithm will be reviewed first to point out clearly problems and causes thereabout which will be caused when trying to expand the two-dimensional reconstruction algorithm to a three-dimensional reconstruction algorithm. A three-dimensional reconstruction algorithm according to the present invention, which has been realized based on the fact that there are such problems and causes, will then be detailed using equations. In the following description, n-th-dimensional image reconstruction means n-th-dimensional inverse Radon transform. To compute this transform involves two-dimensional and three-dimensional Radon data. The two-dimensional Radon data (2D-Radon data), which corresponds to projection data acquired according to X-ray absorbance coefficients within an object to be imaged (i.e., the object P described before, which is true of the following description), is obtained by computing line integral on the object, while the three-dimensional Radon data (3D-Radon data) is obtained by computing area integral on the object.

(1) Review of Two-dimensional Reconstruction Algorithm

First of all, a two-dimensional reconstruction algorithm based on a fan beam will now be reviewed from inventor's point of view. In general, in the two-dimensional data acquisition, data of line integral performed on all the lines passing through or being tangent to a two-dimensionally distributed object becomes two-dimensional Radon data (i.e., X-ray projection data). Acquiring such a two-dimensional Radon data will lead to a complete reconstruction. This will now be described in connection with FIGS. 4 to 19. For the sake of simplifying the following description, an assumption is made such that the X-ray detector is formed into an arc-type of detector, in which the detection elements are arranged at equal intervals along an arc so that equi-angular sampling is possible. However, as described above, in the present invention, the shape itself of the detector (i.e., arc-type or linear-type) is not a significant issue.

Figure 4:
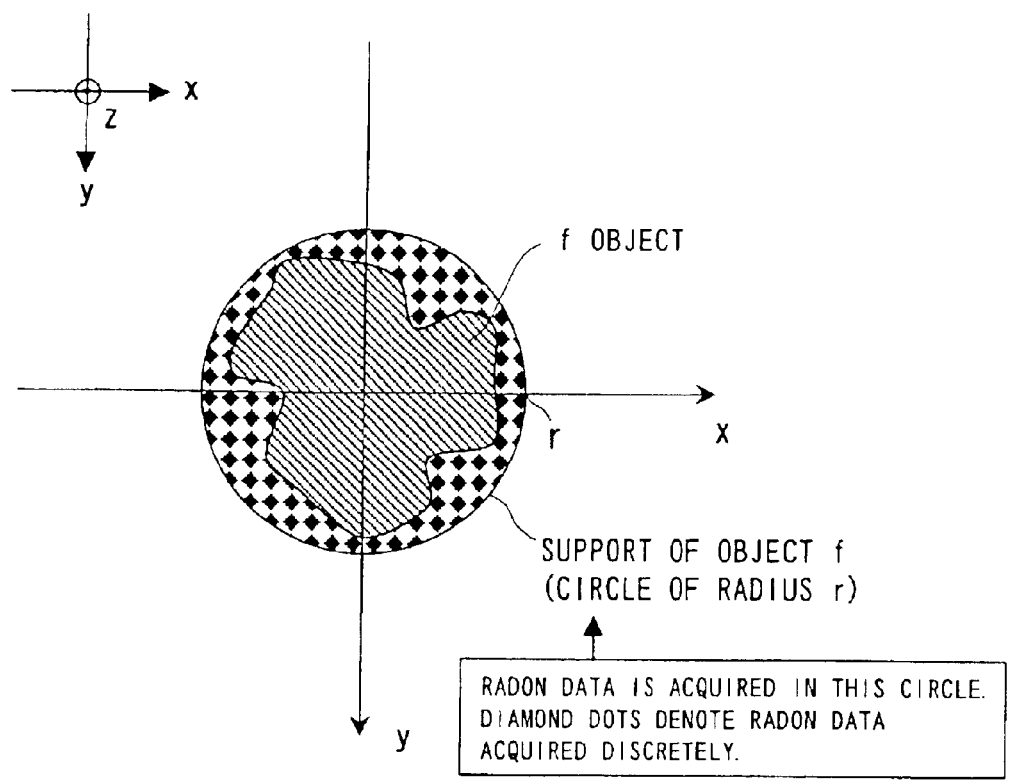
FIG. 4 explains two-dimensional data acquisition in the coordinate space.

First, as shown in FIG. 4, a virtual x-y coordinate is introduced, wherein the rotation axis (rotation center) z of the foregoing rotation frame 9 placed inside the gantry 1 is set as the origin. Thus, to reconstruct a two-dimensional image of an object f, two-dimensional Radon data should be acquired to be discretely filled in a two-dimensional Radon space defined by a support of radius r of which center axis is the rotation axis z and which includes the object f.

Figure 5:
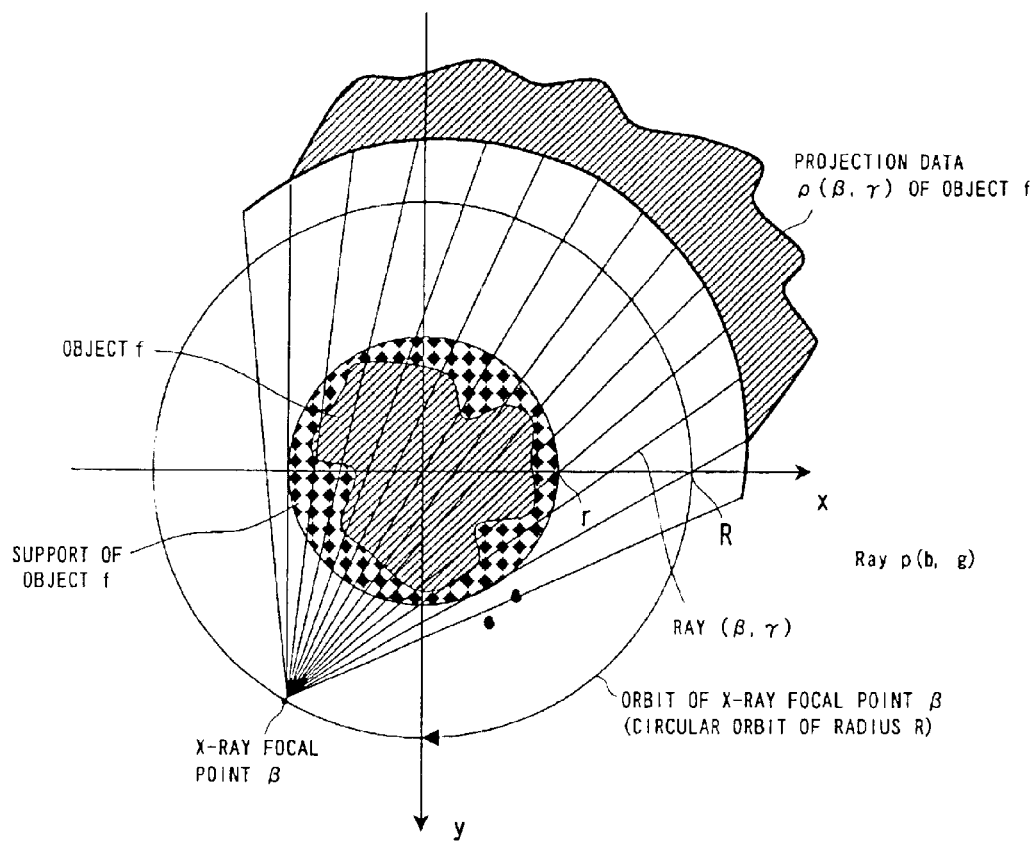
FIG. 5 explains two-dimensional data acquisition in the two-dimensional Radon space.

As shown in FIG. 5, X-ray projection data p of the object f which is acquired by CT or others and which corresponds to the two-dimensional Radon data is composed of an aggregation of values produced by performing line integral on X-ray absorption coefficients of the object f along each ray in a fan beam.

Figure 6:
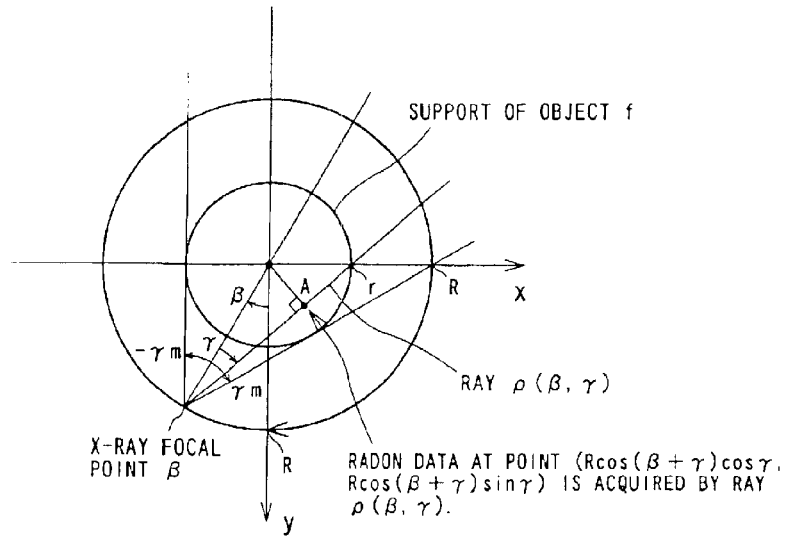
FIG. 6 explains two-dimensional Radon data in the coordinate space.

For instance, as shown in FIGS. 5 and 6, when it is assumed that the X-ray focal point of the X-ray tube 10 is forced to rotate along an circular orbit whose radius is R and whose center is the rotation axis z, the acquisition of projection data $p(\beta,\gamma)$ of the object f along each ray extending from the X-ray focal point $\beta$ on the circular orbit is identical to, in the two-dimensional Radon space, acquisition of two-dimensional Radon data at an intersection A made by drawing a line perpendicular to the ray from the rotation axis z. (In this projection data, $\beta$ is a projection angle, i.e., a position of the X-ray focal point and $\gamma(-\gamma m$ to $\gamma m)$ is a ray angle.)

Figure 7:
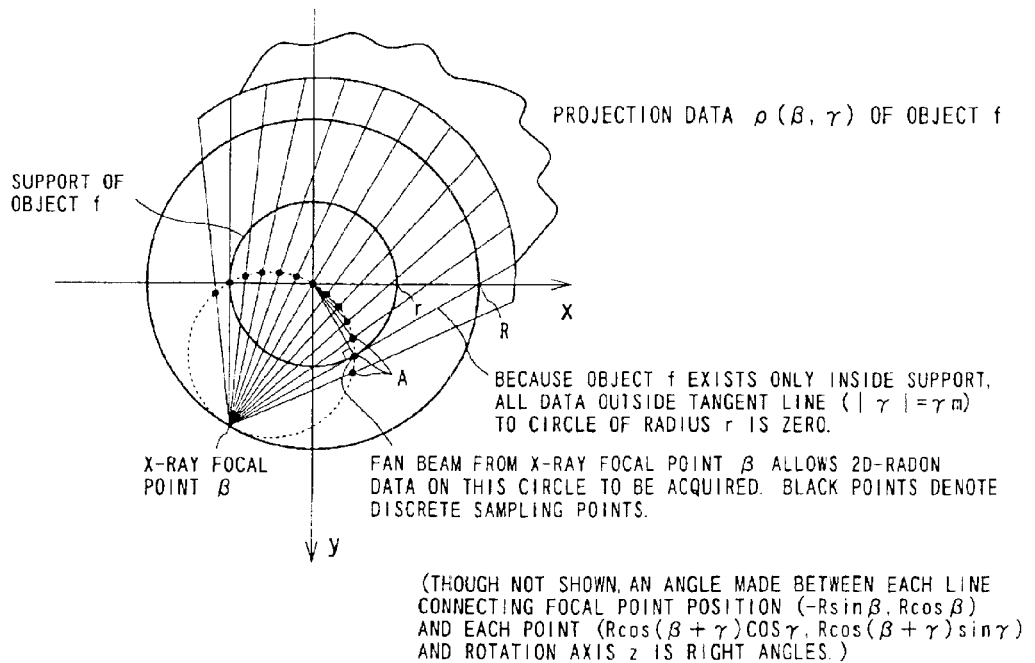
FIG. 7 explains a mass of two-dimensional Radon data to be acquired by a fan beam radiated from an X-ray focal point in the coordinate space.

Accordingly, as shown in FIG. 7, when the projection data $p(\beta,\gamma)$ of the object f is acquired along all the rays radiated from the X-ray focal point $\beta$, two-dimensional Radon data can be acquired along a circle (refer to solid lines and a dotted line in FIG. 7) whose diameter is a length extending from the X-ray focal point $\beta$ to the rotation axis z. In this case, if a spread (fan angle) of the elements of the detector is limited due to their discrete arrangement, two-dimensional Radon data can be acquired in a range limited by solid lines shown in FIG. 7.

Figure 8:
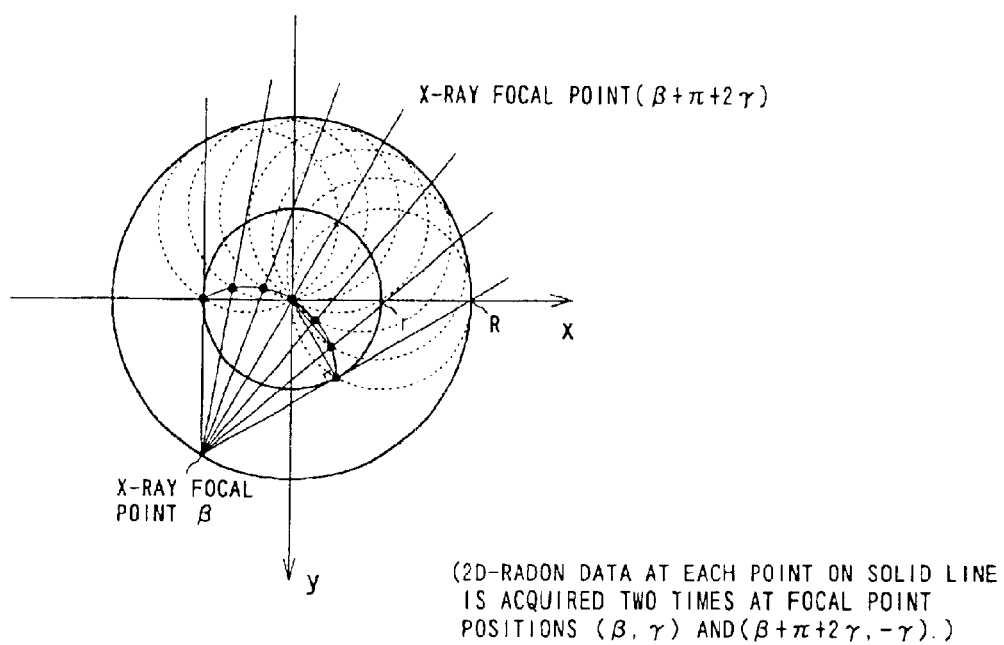
FIG. 8 explains redundant acquisition of two-dimensional Radon data.
Figure 9:
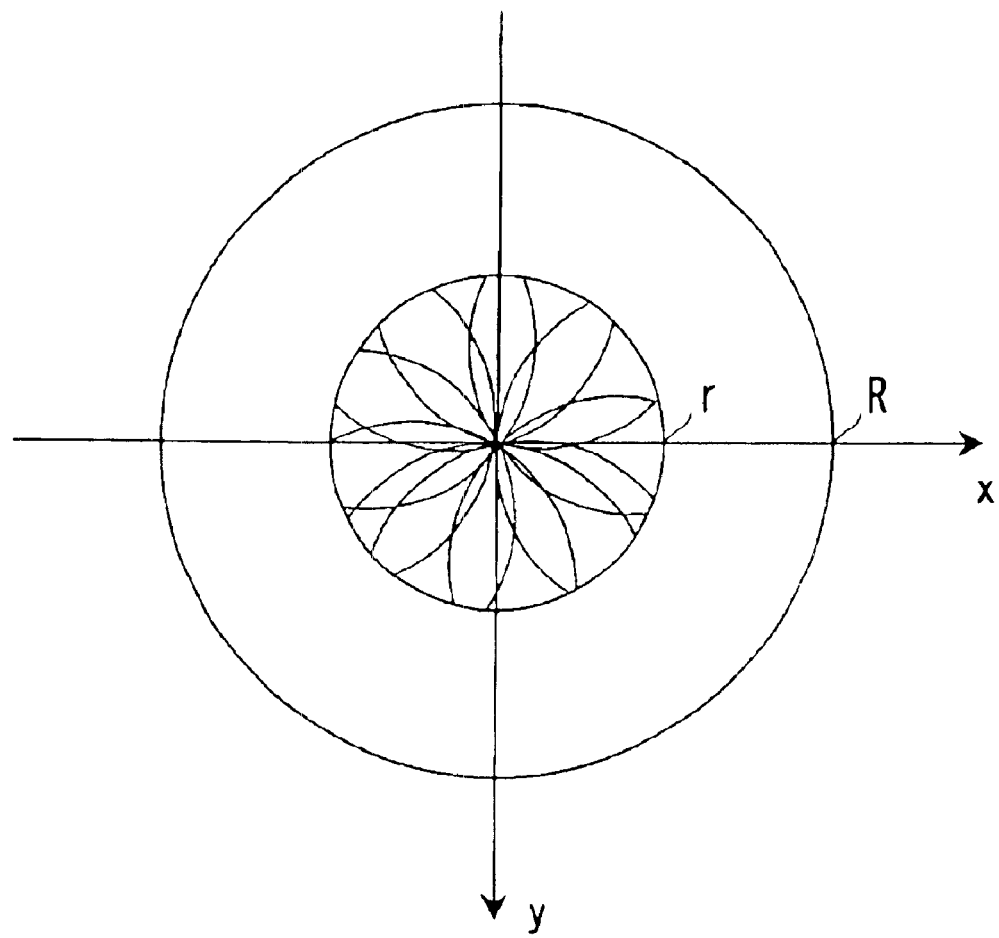
FIG. 9 explains redundant acquisition of two-dimensional Radon data in the coordinate space.

Thus, as shown in FIGS. 8 and 9, when scanning is made while the X-ray focal point $\beta$ is rotated one time along a circular orbit of radius R on the plane at z=0 around the rotation axis z, the two-dimensional Radon data is acquired two times at the same point A. This means that the data acquisition in this scanning is redundant.

Figure 10:
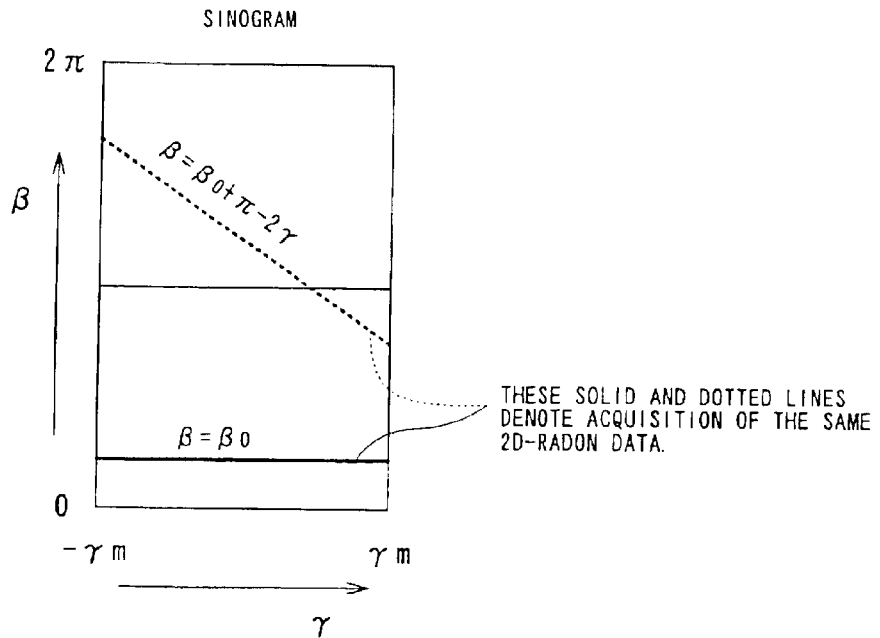
FIG. 10 explains redundant acquisition of two-dimensional Radon data in a sinogram.

FIG. 10 shows a sinogram where a lateral axis denotes a ray angle $\gamma(-\gamma m$ to $\gamma m)$ and a longitudinal axis denotes a projection angle β(0 to 2π) corresponding to the positions of the X-ray focal point. This sinogram explains the foregoing data acquisition. For example, two-dimensional Radon data obtained at β=β₀ shown by a solid line and two-dimensional Radon data obtained at β=π+2γ shown by a dotted line are equal to each other.

An algorithm to reconstruct an image of the object f from two-dimensional Radon data (projection data) obtained by a scan traced along a two-dimensional circular orbit described above will now be explained.

First, a reconstruction algorithm based on a two-dimensional circular-orbit full scan (hereafter, occasionally abbreviated as "FS (Full Scan)") will now explained. This reconstruction algorithm uses a technique of giving equally weighting to mutually redundant data of the two-dimensional Radon data obtained by a one-rotation scan. This weighting can be expressed by the following equations (1) to (5):

$$w(\beta,\gamma)=w(\beta+\pi+2\gamma,-\gamma)=\tfrac{1}{2}, \quad \text{Eq.(1)}$$

$$f(x,y) = \int_0^{2\pi} \frac{R}{L^2(\beta,x,y)} \quad \text{Eq. (2)}$$
$$\int_{-\gamma_m}^{\gamma_m} [w(\beta,\gamma)\cdot p(\beta,\gamma)]\cdot g(\gamma'-\gamma)\cdot\cos\gamma\,d\gamma\,d\beta,$$

$$g(\gamma) = \left(\frac{\gamma}{\sin\gamma}\right)^2 h(\gamma), \quad \text{Eq. (3)}$$

$$h(t) = \int_{-\infty}^{\infty} |\varpi|e^{j2\pi\varpi t}d\varpi \quad \text{Eq. (4)}$$

$$L^2(\beta,x,y)=(R\sin\beta+x)^2+(R\cos\beta-y)^2 \quad \text{Eq.(5)}$$

In the above equation (1), w(β,γ) denotes a function used for the weighting. The equations (2) to (5) relate to fan-beam reconstruction based on an equiangular data acquisition technique, in which f(x,y) is data to be reconstructed of the object f, g(γ) is a function used for filtering, h(t) is a function used for computing the function g(γ), and L²(β, x, y) is a function used for inverse projection, respectively.

Further, the equation (1) indicates the weighting. This reconstruction algorithm is based on two-dimensional inverse Radon transform, which is able to reconstruct a sectional image of the object f with precision.

The above will now be explained conceptually. First, projection data p(β,γ) acquired at an arbitrarily-positioned X-ray focal point β along a circular orbit is weighted by cos γ and the function w(β,γ) in the above equations (step 1), the weighted projection data is filtered by the function g(γ) in the above equations (step 2), and as the filtered data is weighted by L⁻² (β, x, y) in the above equations, fan-beam inverse projection is carried out (step 3). The processing based on the steps 1 to 3 is repetitively applied to each of all the focal point positions β along the circular orbit enables an image of the object f to be reconstructed (step 4).

This reconstruction algorithm can be used on the assumption that 1) the object f is stationary or its movement is as small as negligible; 2) a CT scanner is fully stable in its mechanical characteristics and geometric error in the acquisition position is negligible; 3) the influence of scattered rays in the object f is negligible; and 4) the influence resulting from the fact that the sizes of the X-ray focal point β and each detection element are finite (that is, the positions are changed to each other) is negligible.

As a result, in performing this reconstruction algorithm, it is possible to equally weigh redundant data, as can be expressed by the equation (1), thus the error due to noise can be minimized. The reason is that two opposed rays (refer to FIGS. 8 and 9) subjected to acquisition at different focal point positions β give the same line-integral value, except photon noise, under the foregoing assumptions.

Figure 11:
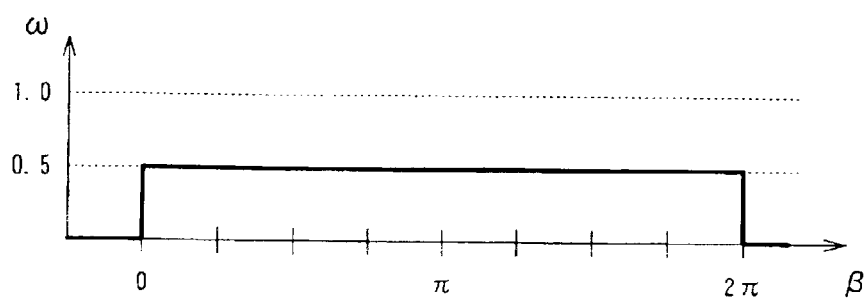
FIG. 11 shows a temporal sensitivity profile of a slice image obtained by performing a two-dimensional circular-orbit full scan (FS)
Figure 12:
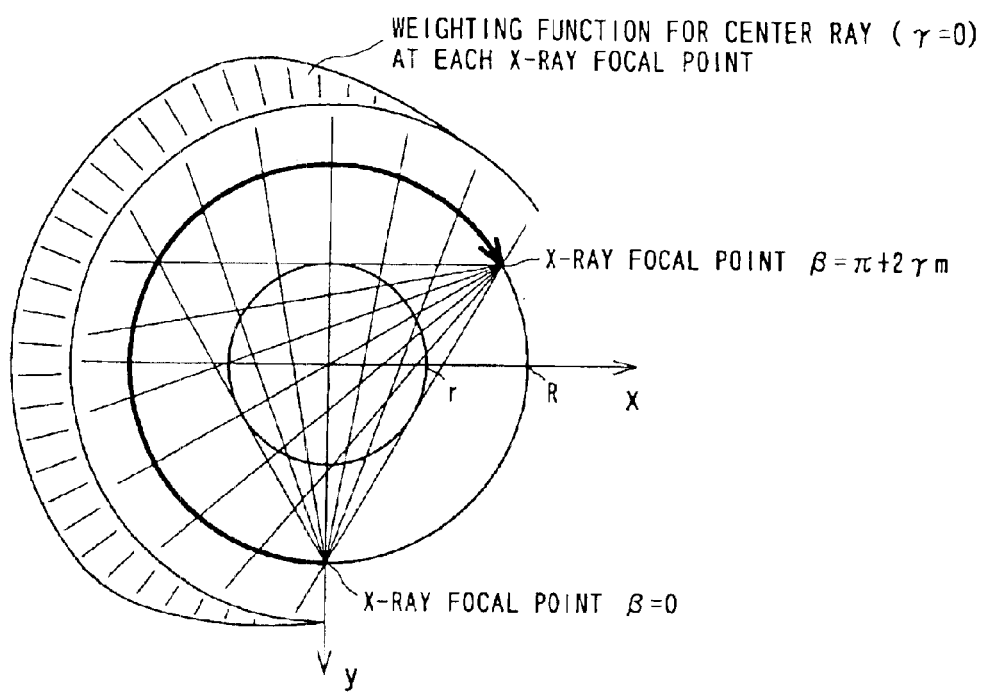
FIG. 12 explains reconstruction in performing a two-dimensional circular-orbit half scan (HS)

FIG. 11 illustrates a temporal sensitivity profile with respect to a slice image of the object f, which is obtained by the foregoing circular-orbit full scan FS. In the profile, the lateral axis denotes the focal point position β corresponding to time, while the longitudinal axis denotes the weighting function w. In FIG. 11, temporal resolution (equal to a half bandwidth of the profile) is the same as T required for one-time rotation of the X-ray focal point β.

A reconstruction algorithm based on a two-dimensional circular-orbit half scan (hereafter, occasionally abbreviated as "HS (Half Scan)") will now explained. The circular-orbit half scan HS takes it into account the fact that, as stated above, the circular-orbit full scan FS involving a one-rotation scan is accompanied by redundant acquisition of two-dimensional Radon data. Hence, the circular-orbit half scan HS is directed to minimizing redundant data acquisition, and scans an angular range covered by half a rotation plus a little extra angular range (i.e., π+2γm).

In the reconstruction algorithm based on this circular-orbit half scan HS, a function w(β,γ) used for the weighting is set such that partially redundant data undergoes "a weighting function that is continuous in a view direction β and a ray direction γ." This weighting can be formulated by the following equations (11) to (14):

$$w(\beta,\gamma)+w(\beta+\pi 2\gamma,-\gamma)=1, \quad \text{Eq.(11)}$$

$$w[x(\beta,\gamma)]=3x^2(\beta,\gamma)-2x^3(\beta,\gamma), \quad \text{Eq.(12)}$$

$$x(\beta,\gamma) = \begin{cases} \dfrac{\beta}{2\gamma_m+2\gamma} & 0\le\beta\le 2\gamma_m+2\gamma \\ 1 & 2\gamma_m+2\gamma<\beta<\pi+2\gamma. \\ \dfrac{\pi+2\gamma_m-\beta}{2\gamma_m-2\gamma} & \pi+2\gamma\le\beta\le\pi+2\gamma_m \end{cases} \quad \text{Eq. (13)}$$

$$f(x,y) = \int_0^{2\pi} \frac{R}{L^2(\beta,x,y)} \quad \text{Eq. (14)}$$
$$\int_{-\gamma_m}^{\gamma_m} [w(\beta,\gamma)\cdot p(\beta,\gamma)]\cdot g(\gamma'-\gamma)\cdot\cos\gamma\,d\gamma\,d\beta,$$

As can be understood from the equation (14) to obtain f(x,y), the range to the focal point position β is replaced by [0, π+2γm], not [0, 2π] as shown in the foregoing equation (2). In this case, within β∈[π+2γm, 2π], the foregoing equation (2) may be used, without any changes, instead of the equation (13), on condition that x²(β,γ)=w(x²β,γ))=0 is maintained.

Figure 13:
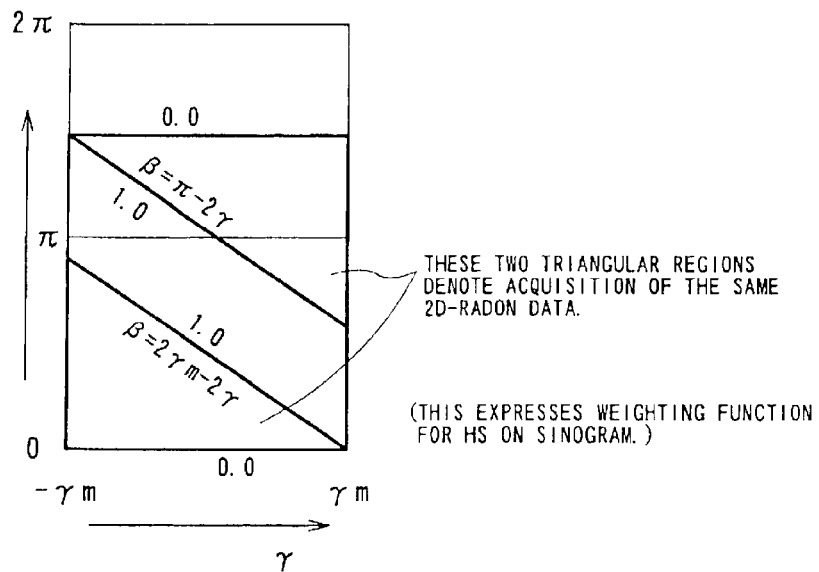
FIG. 13 is an explanation of two-dimensional Radon data in the sinogram, which is applied to the HS reconstruction.
Figure 14:
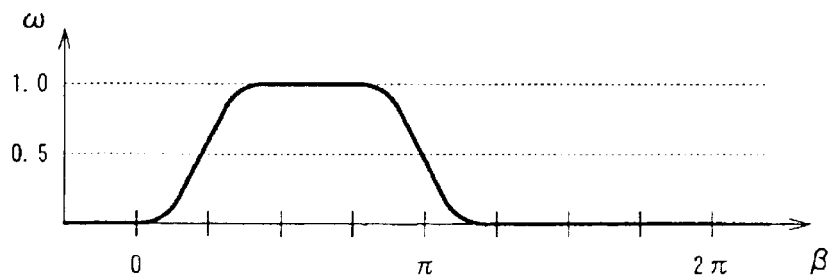
FIG. 14 explains a temporal sensitively profile of a slice image applied to the HS reconstruction.
Figure 15:
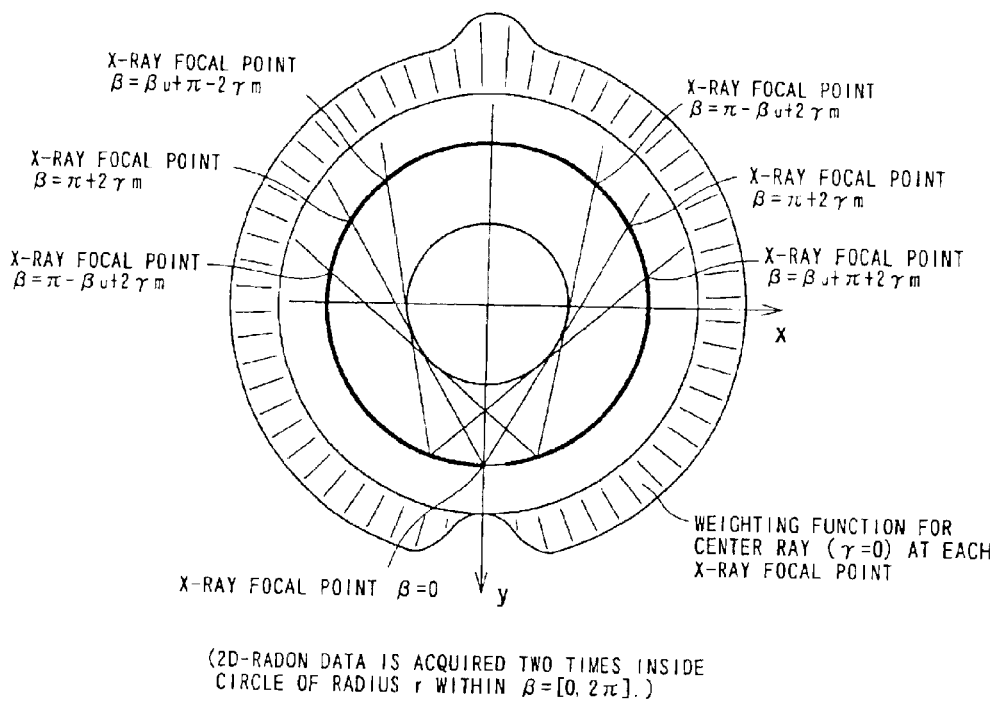
FIG. 15 is an explanation of reconstruction applied to a two-dimensional circular-orbit under scan (US)

FIG. 13 conceptually explains the reconstruction algorithm based on the foregoing half scan HS, FIG. 14 shows a sinogram of the half scan HS, and FIG. 15 illustrates a temporal sensitivity profile at a central part in a slice image obtained under this half scan HS, respectively.

In FIG. 13, an arch-like graph shown outside the circular orbit shows a weight to a central ray (γ=0) at each X-ray focal point position (each projection angle). For instance, since, at the X-ray focal point β=0, all data are acquired twice by both the rays radiating from the point β=0 and the rays opposed to the rays radiating from the point β=0, a weight is set to zero. In the case of X-ray focal points shifted from the point β=0, most rays are subjected to two-time data acquisition, but part of the rays is subjected to only one-time acquisition carried at just the X-ray focal points generating the part of the rays. Thus, a weight for the rays experiencing only one-time acquisition is assigned to 1. Meanwhile, in order to change weights in a smooth manner, a weight for each of the rays experiencing two-time acquisition is assigned by both the foregoing equation (11) and a rule representing "a weighting function that is continuous in a view direction β and a ray direction γ."

According to both the above scan and the above reconstruction algorithm, the region of projection angles for image reconstruction, that is, a data acquisition time is reduced down to about half a data acquisition time needed for the one-rotation scan. Hence, the temporal sensitive profile shown in FIG. 14 is obtained at a central part of a slice image, so that the temporal resolution is improved up to T/2. This is consistent with the graph for the weighting in FIG. 12 and results shown by the sinogram in FIG. 13. In return for improving the temporal resolution as stated above, the number of projections required for reconstructing images (that is, the number of data, i.e., the number of photons) is reduced to almost half of the number of projections obtained by the foregoing circular-orbit full scan FS, resulting in that image noise rises about 1.4 times as much as the full scan FS.

Incidentally, as to the foregoing "a weighting function that is continuous in a view direction β and a ray direction γ," the continuity can be complemented in terms its significance as follows. The computation for the reconstruction shown by the foregoing equations (2) and (14) involves convolution to enhance a higher-frequency region in the ray direction. Hence, if the data weighted by the convolution has discontinuity in the ray direction, this discontinuity will be exaggerated more than necessary, whereby the exaggerated discontinuity will be left as artifacts in a final image (i.e., a reconstructed image). It is therefore required that the weighting function be continuous in the ray direction, except the discontinuity attributable to discontinuous distributions of an X-ray absorption coefficient or others, which are inherent to the object f.

In addition, the foregoing two-dimensional circular-orbit half scan HS can be expanded conceptually. To be specific, a virtual fan angle 2Γm is introduced instead of 2γm and the projection angles for the reconstruction are set to a range of π+2γm to 2π, which leads to a reconstruction algorithm known as a two-dimensional circular-orbit modified half scan (hereafter, occasionally abbreviated as "MHS (Modified Half Scan)") (refer to M. D. Silver: "A method for including redundant data in computed tomography," Med. Phys. 27, pp.773–774, 2000). Even in this algorithm, the temporal resolution achieves T/2.

Reconstruction based on a two-dimensional circular-orbit under scan (hereafter, occasionally abbreviated as "US (Under Scan))" will now be described.

Both data acquired at X-ray focal points at both the acquisition start time (β=0, t=0) and the acquisition end time (β=2π, t=T) in the one-rotation scan under the full scan FS mutually get very closed in the two-dimensional Radon space. However, if an object moves during a one-rotation scan, one of the above-listed assumptions for reconstruction, that is, the condition that "the object f is stationary or its movement is as small as negligible" will not be met, both of the data acquired at the acquisition start and end times become shifted largely with each other on account of the motion of the object f. Hence, when the full scan FS is carried out, inconsistency arises in data, so that an artifact spreading in a fan form from a focal point of j=0 will appear in a reconstructed image.

Considering this drawback, the reconstruction based on the two-dimensional circular-orbit under scan US is directed to suppression of the artifact emerging due to motion of an object. To realize this, together with the foregoing equation (2) for the reconstruction for FS, the following equations (21) and (22) are added to the weighting equations.

$$w(\beta,\gamma)+w(\beta+\pi+2\gamma,-\gamma)=1, \qquad \text{Eq.(21)}$$

$$w(\beta,\gamma) = \begin{cases} \dfrac{3x^2-2x^3}{2} & \text{where } x=\dfrac{\beta}{\beta_u} & 0 \leq \beta \leq \beta_u \\[4pt] \dfrac{1}{2} & & \beta_u < \beta \leq \pi-\beta_u+2\gamma \\[4pt] 1-\dfrac{3x^2-2x^3}{2} & \text{where } x=\dfrac{|\beta-\pi-2\gamma|}{\beta_u} & \pi-\beta_u+2\gamma < \beta \leq \pi+\beta_u+2\gamma. \\[4pt] \dfrac{1}{2} & & \pi+\beta_u+2\gamma < \beta \leq 2\pi-\beta_u \\[4pt] \dfrac{3x^2-2x^3}{2} & \text{where } x=\dfrac{2\pi-\beta}{\beta_u} & 2\pi-\beta_u < \beta \leq 2\pi \end{cases} \qquad \text{Eq. (22)}$$

Figure 16:
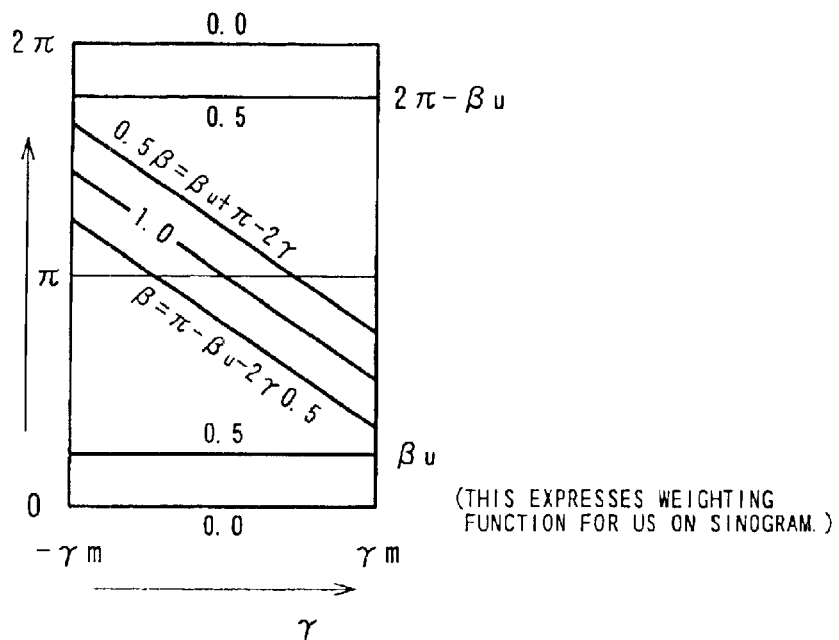
FIG. 16 is an explanation of two-dimensional Radon data in the sinogram, which is applied to the US reconstruction.
Figure 17:
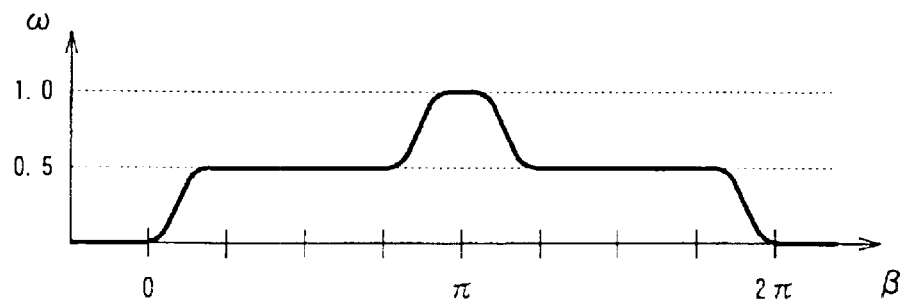
FIG. 17 explains a temporal sensitively profile of a slice image applied to the US reconstruction.

FIG. 15 conceptually explains the reconstruction based on the foregoing circular-orbit under scan HS, FIG. 16 shows a sinogram for the scan, and FIG. 17 is a temporal sensitivity profile at a central part of a slice image obtained by the scan, respectively.

In FIG. 15, a circular graph shown outside the circular orbit shows a weight to a central ray (γ=0) at each X-ray focal point position (each projection angle). As shown in FIGS. 15 to 17, in the circular-orbit under scan HS, the weights are decided so as to remove the consistency in the data provided by the foregoing FS. Specifically, the lower the reliability of data (β=0, 2π or thereabouts), the lower the weights are, while still maintaining the continuity of the weights, so that the data mapped in a necessary two-dimensional Radon space becomes uniform in values.

Reconstruction based on a two-dimensional circular-orbit over scan (hereafter, occasionally abbreviated as "OS (Over Scan))" will now be described. This scan is directed to the same purpose as that for the under scan, in which the scan is conducted to cover both an angular range of one rotation and a little extra angular range and two projection data acquired twice at the same projection angle (i.e., the same focal point position) before and after one rotation of the focal point are processed by individually weighting different weights to those data. After such weighting which can be summarized by the following equations, a reconstruction algorithm is applied to the data in the similar manner to the foregoing FS.

$$w(\beta, \gamma) = \begin{cases} \dfrac{3x^2 - 2x^3}{2} & \text{where } x = \dfrac{\beta}{\beta_0} & 0 \le \beta \le \beta_0 \\ \dfrac{1}{2} & & \beta_0 < \beta \le 2\pi \\ 1 - \dfrac{(3x^2 - 2x^3)}{2} & \text{where } x = \dfrac{2\pi + \beta_0 - \beta}{\beta_0} & 2\pi < \beta \le 2\pi + \beta_0 \end{cases} \quad \text{Eq. (23)}$$

Figure 18:
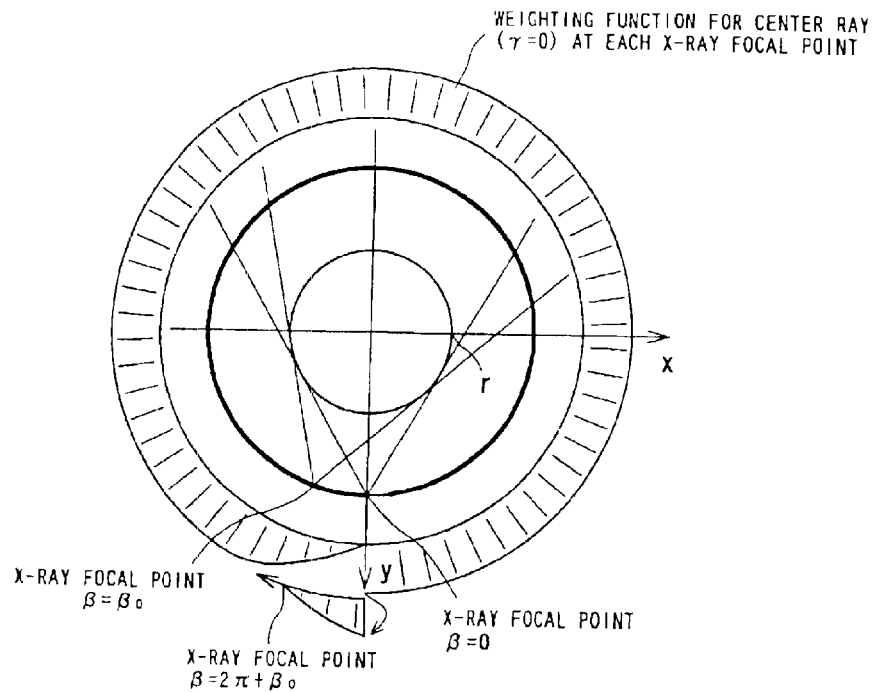
FIG. 18 is an explanation of reconstruction applied to a two-dimensional circular-orbit over scan (OS)
Figure 19:
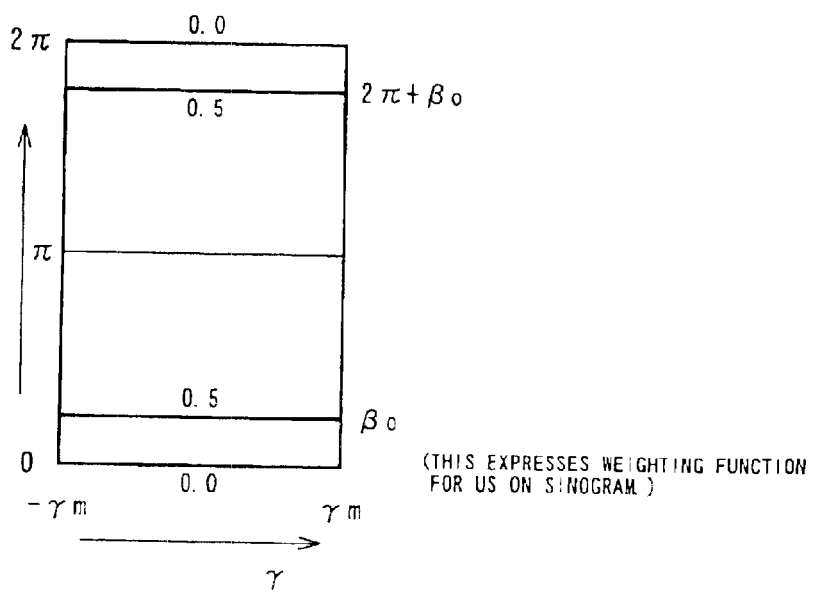
FIG. 19 is an explanation of two-dimensional Radon data in the sinogram, which is applied to the OS reconstruction.

FIG. 18 conceptually explains the reconstruction algorithm based on the foregoing circular-orbit over scan OS. FIG. 19 shows a sinogram of the scan, in which there is shown a circular graph outside the circular orbit. This graph shows a weight to a central ray ($\gamma=0$) at each X-ray focal point position (each projection angle). As shown in FIGS. 18 and 19, the temporal resolution for this can become T.

(2) Review of Three-dimensional Reconstruction Algorithms and Problems Thereof.

From an inventor's point of view, known three-dimensional reconstruction algorithms will now be reviewed based on the results derived from reviewing the foregoing two-dimensional reconstruction algorithms, so that some problems of those three-dimensional reconstruction algorithms will be made clear. In this review, an assumption is made such that either a cylindrical type of detector (in which detection elements are arranged on a cylindrical plane at equal pitches and an x-y plane is subjected to equiangular sampling in a ray direction and equidistance sampling in the z-axis direction) or an area type of detector (in which detection elements are arranged on the detector plane at equal pitches and the plane is subjected to equidistance sampling) will be used so as to be convenient for each review, depending on each algorithm.

Figure 20:
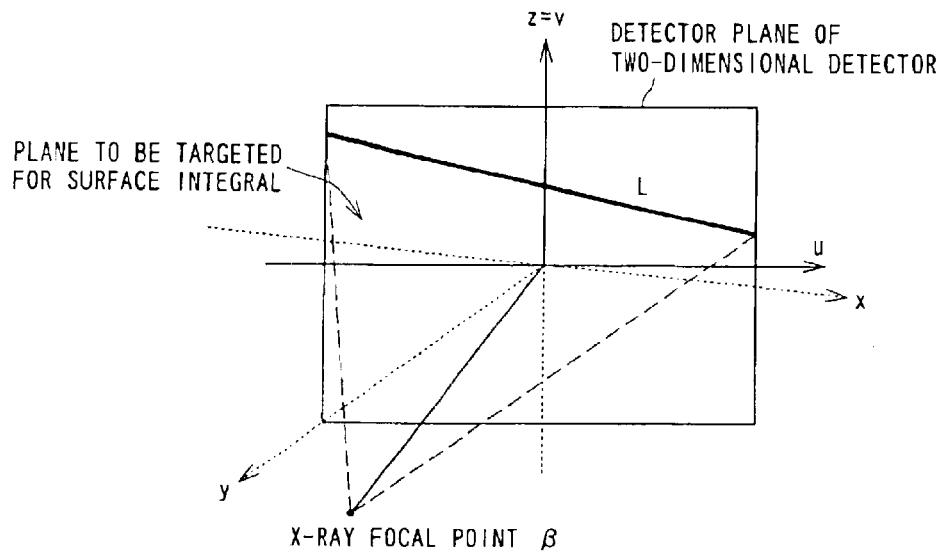
FIG. 20 explains three-dimensional data acquisition in the coordinate space.
Figure 21:
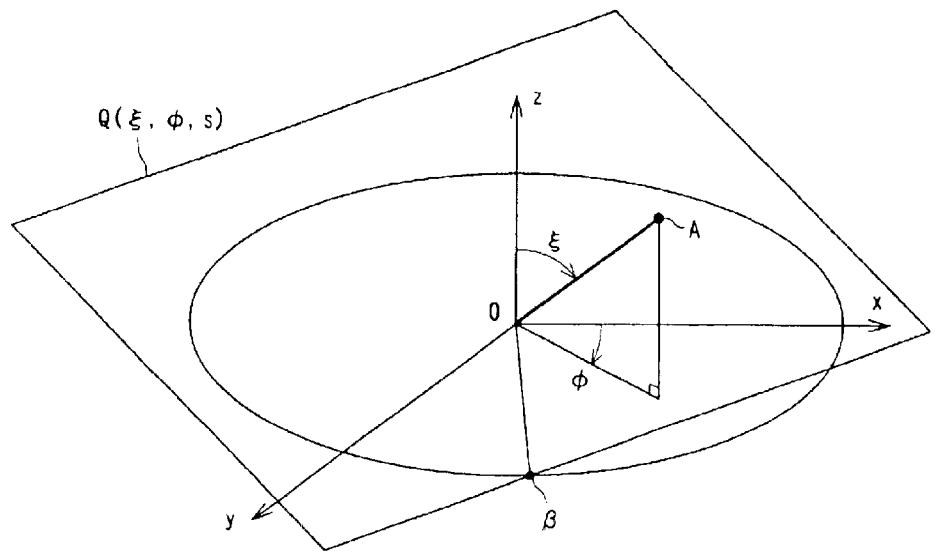
FIG. 21 explains three-dimensional data acquisition in the three-dimensional Radon space.

FIGS. 20 and 21 show a concept for three-dimensional data acquisition carried out in the three-dimensional coordinate. As shown in FIGS. 20 and 21, the three-dimensional data acquisition is identical to acquisition of three-dimensional Radon data ($\eta,\phi,s$) at a point A in the three-dimensional Radon space (refer to FIG. 21) by processing an integral value figured out through area integral of projection data $p(\beta,\gamma,\alpha)$ projected from an X-ray focal point $\beta$ (not shown), along a plane (for example, a straight line L on the area detector shown in FIG. 20) that includes both of the X-ray focal point $\beta$ and a plane Q targeted to the area integral. $\beta$ denotes a projection angle (indicative of the position of the X-ray focal point), $\gamma$ denotes a ray angle, and $\alpha$ denotes a cone angle (i.e., angle made between the x-y plane and each ray), respectively.

Figure 22:
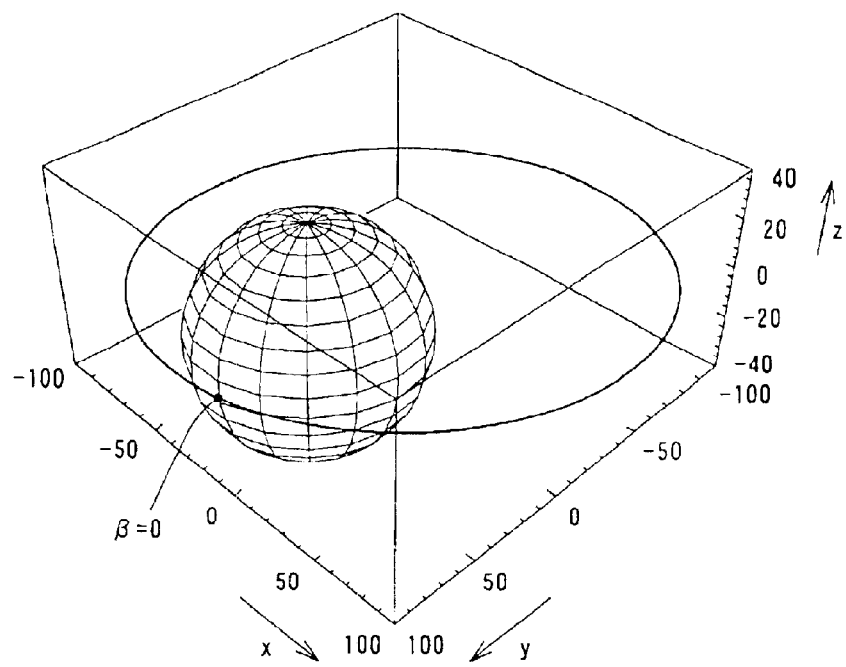
FIG. 22 explains three-dimensional Radon data acquired using a cone beam radiated from a focal point.

Accordingly, as shown in FIG. 22, using all the rays of a cone beam radiated from the position of each X-ray focal point $\beta$, three-dimensional Radon data mapped on the surface of a sphere can be acquired, the diameter of the sphere being a length connecting each X-ray focal point $\beta$ and the center $O(x=0, y=0, z=0)$ of the coordinate system. In this acquisition, a manner similar to the foregoing two-dimensional case may be assumed. That is, when it is assumed that the detection elements are discretely disposed and have a limited spread (fan angle), data of only a certain limited area on the sphere is acquired.

Figure 23:
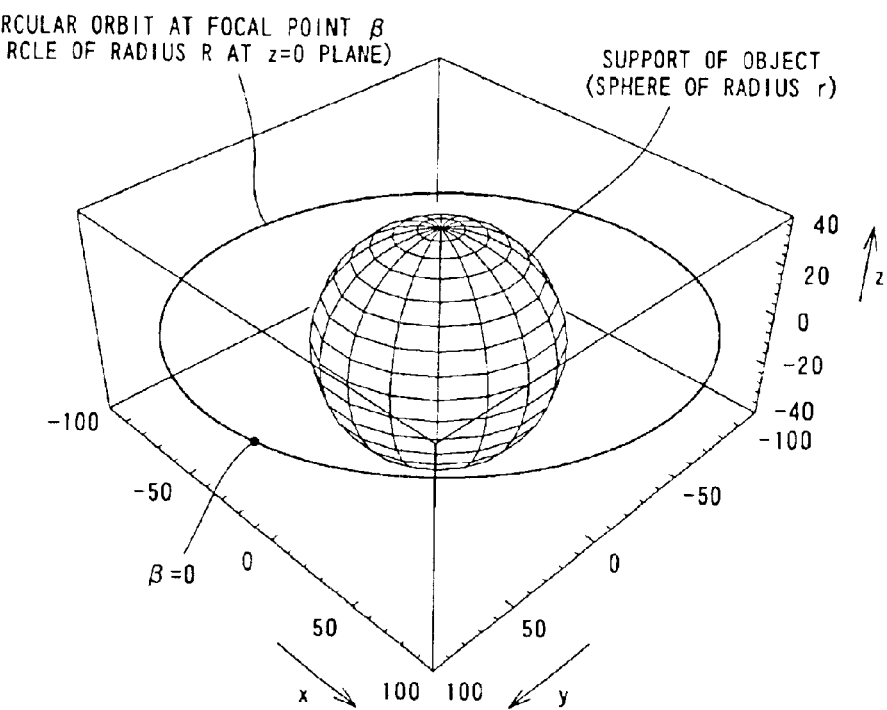
FIG. 23 is an explanation of three-dimensional Radon data necessary for reconstructing an object to be imaged.

Incidentally, as shown in FIG. 23, when it can be assumed that a support for an object is formed into a sphere having a radius r, an exact three-dimensional reconstruction requires that area-integral values of all of the surfaces crossing the sphere or being tangent to the sphere be figured out.

Based on the above outline of the three-dimensional data acquisition, a three-dimensional reconstruction algorithm will now be described.

First of all, a reconstruction algorithm using a three-dimensional circular-orbit full scan FS will now be described. This algorithm is realized by simply expending the foregoing two-dimensional FS reconstruction algorithm to the three-dimensional one. To be specific, this algorithm is originated by extending Feldkamp reconstruction algorithm, which has originally developed into an area detector (in which detection elements are desposed on the detector plane at equal pitches and subjected to equidistance sampling), to a cylindrical type of detector. Feldkamp reconstruction algorithm is known by "L. A. Feldkamp, L. C. Davis, and J. W. Kress: "Practical cone-beam algorithm," J. Opt. Soc. Am., 1(6), pp. 612–619, 1984." Such an extended algorithm is known by "H. Kudo and T. Saito: "Three-dimensional helical-scan computed tomography using cone-beam projection," IEICE(D-II) J74-D-II, 1108–1114 (1991)." To differentiate from the two-dimensional FS, this extended algorithm will be occasionally abbreviated as "Feldkamp+FS."

Reconstruction based on the three-dimensional circular-orbit full scan FS can be detailed such that, of the three-dimensional Radon data (projection data) acquired by a one-rotation scan, mutually redundant data undergoes weighting carried out at equal weights, which can be expressed by the following equations (31) to (35).

$$w(\beta,\gamma,\alpha)=w(\beta+\pi+2\gamma,-\gamma,\alpha)=\tfrac{1}{2}, \quad \text{Eq.(31)}$$

$$f(x, y, z) = \int_0^{2\pi} \frac{R}{L^2(\beta, x, y)} \int_{-\gamma_m}^{\gamma_m} [w(\beta, \gamma, \alpha) \cdot p(\beta, \gamma, \alpha)] \cdot g(\gamma' - \gamma) \cdot \cos\gamma \cdot \cos\alpha\, d\gamma\, d\beta, \quad \text{Eq. (32)}$$

$$g(\gamma) = \left(\frac{\gamma}{\sin\gamma}\right)^2 h(\gamma), \quad \text{Eq. (33)}$$

$$h(t) = \int_{-\infty}^{\infty} |\varpi| e^{j2\pi\varpi t} d\varpi \quad \text{Eq. (34)}$$

$$L^2(\beta,x,y)=(R \sin \beta+x)^2+(R \cos \beta-y)^2 \quad \text{Eq.(35)}$$

When comparing these equations (31) to (35) with the foregoing equations (equations (1) to (5)) for the two-dimensional FS, the former equations are totally the same as the latter ones, except for that the integral term for projection angels (inverse projection section) in equation (32) is formed into the three-dimensional inverse projection, instead of the two-dimensional inverse projection, and the term of cos $\alpha$ is newly added to equation (32).

This will now be explained conceptually. First, projection data $p(\beta,\gamma,\alpha)$ acquired at an arbitrary X-ray focal point $\beta$ on a circular orbit is weighted using both cos $\gamma$ cos $\alpha$ and a function $w(\beta,\gamma,\alpha)$ (step 1). The weighted projection data is filtered using a function $g(\gamma)$ appearing in the equations (step 2). As the filtered data is weighted using $L^{-2}(\beta,x,y)$ appearing in the foregoing equations, a three-dimensional cone-beam inverse projection is carried out (step 3). The above steps 1 to 3 are repetitively applied to all the focal points fi on the circular orbit, so that an image of an object f can be reconstructed (step 4).

Figure 24:
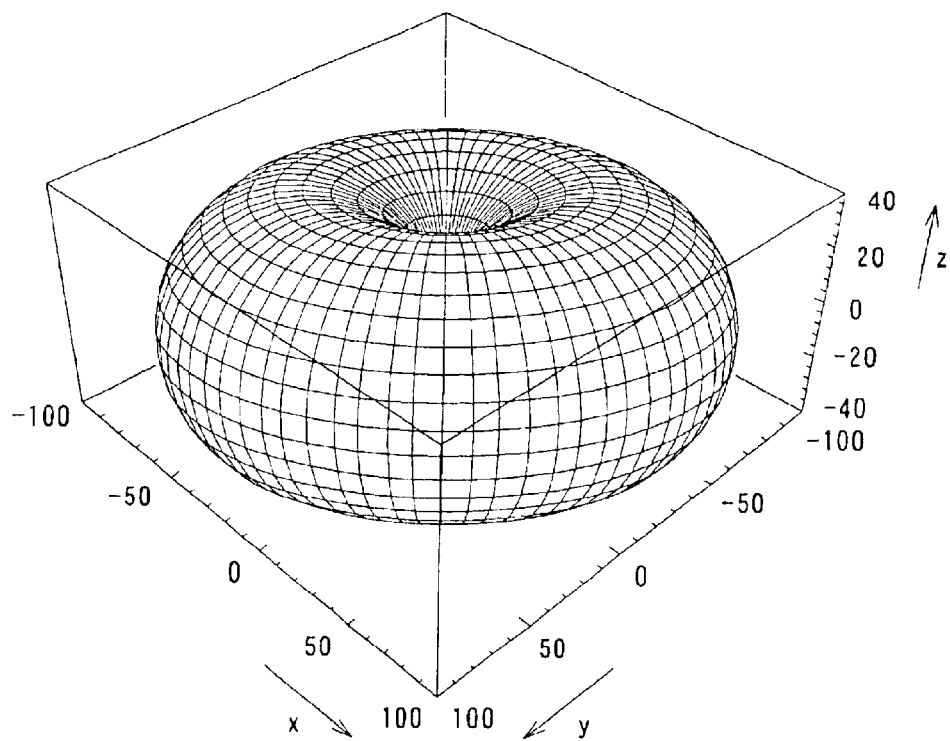
FIG. 24 is an explanation of three-dimensional Radon data acquired through a three-dimensional circular-orbit scan.
Figure 25:
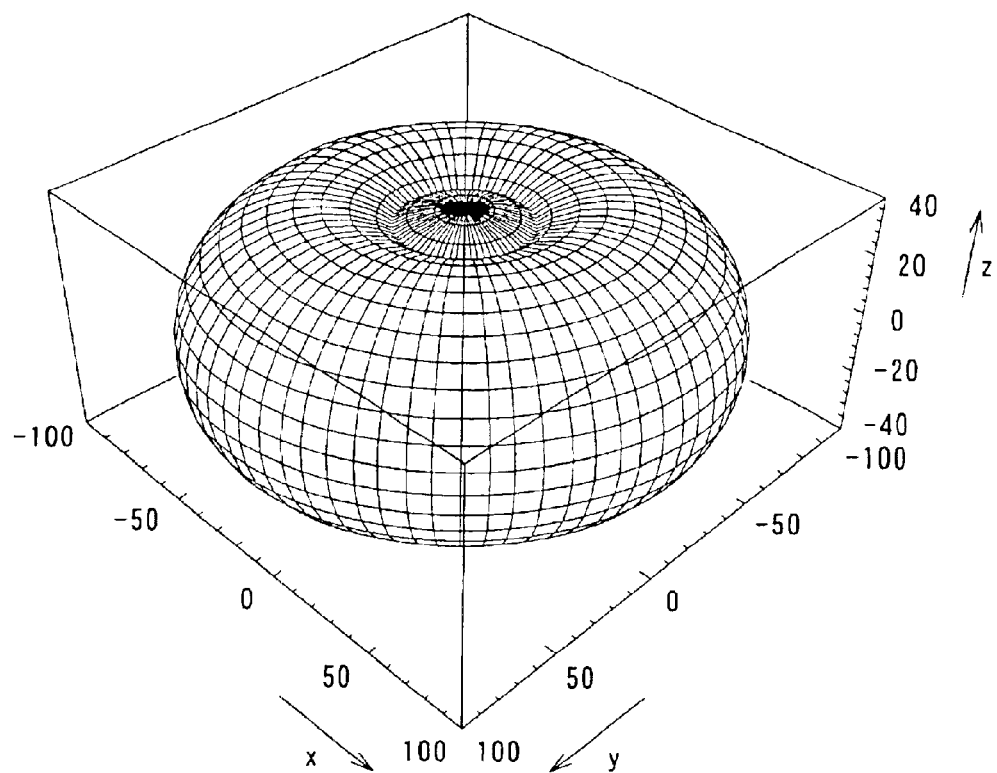
FIG. 25 is a view shown by overlapping the view shown in FIG. 23 and the view shown in FIG. 24 one on the other.

For instance, when a scan is carried out by rotating one time the X-ray focal point along a circular orbit about the rotation axis z on the plane of z=0, three-dimensional Radon data can be acquired twice, as shown in FIG. 24, at each point existing within a region that covers all trajectories formed by rotating one time the sphere (radius r) containing the focal point and the coordinate center (rotation axis), which are described in FIG. 22, about the coordinate center. Such a region is called "apple-like region" for the sake of convenience. Namely, as long as considering the plane of z=0, the data acquisition is carried out redundantly, like the two-dimensional FS.

However, an object to be reconstructed three-dimensionally exists within the sphere (support) having a radius r shown in FIG. 23, thus it is necessary to acquire data within a region containing this sphere. In this respect, since the foregoing three-dimensional "Feldkamp+FS" misses providing all data, resulting in an incomplete scan. This fact is quite obvious when viewing FIG. 25 produced by overlapping FIGS. 23 and 24 one on the other. That is, to reconstruct the support for the object, the "Feldkamp+FS" is insufficient, because this scan does not provide all the three-dimensional data necessary for the reconstruction. Fundamentally, although it is required to acquire data from the entire apple-like region included in the sphere (refer to FIG. 25) in which the object is contained, the data of a core portion of the apple-like region is missed, as shown in FIG. 24. Thus, it is understood that all the necessary three-dimensional data is unable to be acquired. In this case, the data that has not been acquired is sometimes called "missing data."

In addition, a temporal sensitivity profile of a slice image obtained by this three-dimensional "Feldkamp+FS" is similar to the foregoing one shown in FIG. 11.

A reconstruction algorithm based on the three-dimensional circular-orbit half scan will now be explained. In this example, like the above-said three-dimensional "Feldkamp+FS," the algorithm for the two-dimensional scan is extended to the three-dimensional one. Hereafter, this three-dimensional scan is occasionally abbreviated as "Feldkamp+HS," compared to the two-dimensional "HS."

In the three-dimensional "Feldkamp+HS," a scan is performed toward a focal point moved little by little within an angular region along a circular orbit, the angular region corresponding to both of half a rotation and an extra little partial rotation ($\pi+2\gamma m$). Then, the acquired data is weighted with weighting functions to provide continuity in both a view direction and a ray direction. The weights used for this weighting are not produced from a function of a cone angle $\alpha$ (all the detector rows are multiplied by the same weight). This can be expressed by the following equations (41) to (44).

$$w(\beta,\gamma,\alpha)+w(\beta+\pi+2\gamma,-\gamma,\alpha)=1, \quad \text{Eq.(41)}$$

$$w[x(\beta,\gamma),\alpha]=3x^2(\beta,\gamma)-2x^3(\beta,\gamma), \quad \text{Eq.(42)}$$

$$x(\beta, \gamma) = \begin{cases} \dfrac{\beta}{2\gamma_m + 2\gamma} & 0 \le \beta \le 2\gamma_m + 2\gamma \\ 1 & 2\gamma_m + 2\gamma < \beta < \pi + 2\gamma \\ \dfrac{\pi + 2\gamma_m - \beta}{2\gamma_m - 2\gamma} & \pi + 2\gamma \le \beta \le \pi + 2\gamma_m \end{cases} \quad \text{Eq. (43)}$$

$$f(x, y, z) = \int_0^{2\pi} \dfrac{R}{L^2(\beta, x, y)} \int_{-\gamma_m}^{\gamma_m} [w(\beta, \gamma, \alpha) \cdot p(\beta, \gamma, \alpha)] \cdot g(\gamma' - \gamma) \cdot \cos\gamma \cdot \cos\alpha \, d\gamma d\beta, \quad \text{Eq. (44)}$$

Figure 26:
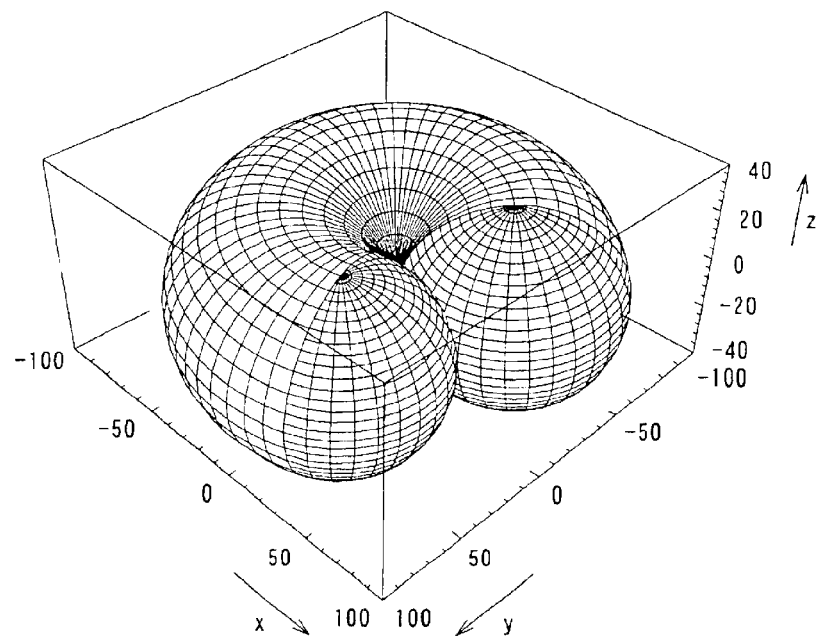
FIG. 26 explains three-dimensional Radon data acquired through a three-dimensional circular-orbit half scan ($\beta$=[0 to $\pi$+2$\pi$m])

FIG. 26 conceptually explains the data acquisition based on the three-dimensional "Feldkamp+HS." As shown in FIG. 26, the three-dimensional Radon data is acquired through scanning within an angular range of $\beta=[0, \pi+2\gamma m]$ along a circular orbit having a radius R about the rotation center axis z on the z=0 plane.

Figure 27:
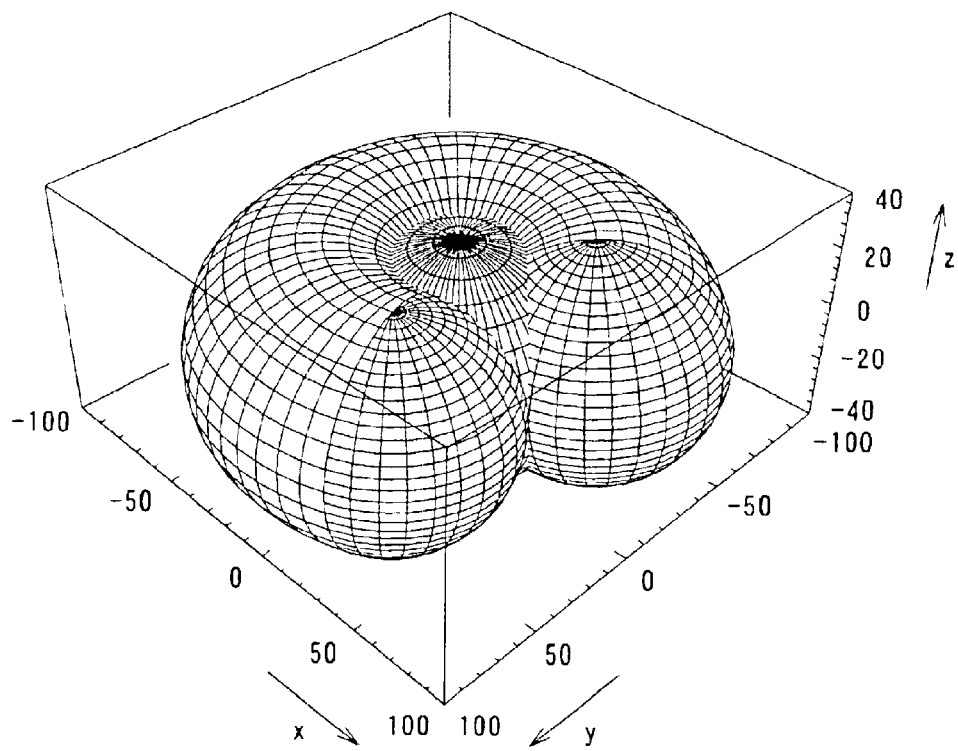
FIG. 27 is a view shown by overlapping the view shown in FIG. 23 and the view shown in FIG. 26 one on the other.

FIG. 27 is shown by overlapping the views shown in FIGS. 23 and 26 one on the other. The comparison between FIG. 27 and FIG. 26 shows that the three-dimensional "Feldkamp+HS" has a wider missing range in the three-dimensional Radon data than the foregoing three-dimensional "Feldkamp+FS." This is due to the fact that the algorithm for the two-dimensional reconstruction is simply extended to the three-dimensional reconstruction. In consequence, although having higher temporal resolution, reconstructed images based on the three-dimensional "Feldkamp+HS" suffer from more artifacts than those reconstructed based on the three-dimensional "Feldkamp+FS," due to the wider data missing region. Therefore, the problem that the three-dimensional "Feldkamp+HS" is off from practical use has been confirmed.

In the case of a Feldkamp+MHS algorithm derived by applying the Feldkamp reconstruction algorithm to the foregoing two-dimensional MHS, an amount of data to be missed is less than that acquired by the "Feldkamp+HS," but the weighting algorithm to correct redundant data acquisition is based on the acquisition positions for the two-dimensional Radon data, not for the three-dimensional Radon data. Thus, like the "Feldkamp+HS," accuracy in the correction becomes lower at positions other than a plane to be scanned.

A reconstruction algorithm based on a three-dimensional circular-orbit under scan US will now be explained. In this algorithm, like the foregoing three-dimensional "Feldkamp+FS," the algorithm based on the two-dimensional US is merely extended to its three-dimensional algorithm. Hereafter, this three-dimensional scan is occasionally abbreviated as "Feldkamp+US," compared to the two-dimensional "US."

This three-dimensional "Feldkamp+US" uses all the data acquired from a scan range of one rotation, but has amounts of missing data greater than that occurring in the "Feldkamp+FS," because weights for part of the data is smaller. In addition, regarding the redundant data acquisition, the weights used for the correction are based on the acquisition positions for the two-dimensional Radon data, not for the three-dimensional Radon data. Thus, there is a problem that, compared to the "Feldkamp+FS," the "Feldkamp+US" suffers from lower accuracy in the correction at positions other than a plane to be scanned.

In case that a reconstruction algorithm based on a three-dimensional circular-orbit over scan US (hereafter, occasionally abbreviated as "Feldkamp+OS"), which is formed by simply extending the two-dimensional circular-orbit over scan OS to its three-dimensional scan, an acquisition rate of three-dimensional Radon data is equal to that of the three-dimensional "Feldkamp+FS," while the temporal resolution is T which is the same as that in the FS. That is, the temporal resolution is not sufficiently higher.

In addition to the various three-dimensional reconstruction algorithms above listed, another algorithm called "Grnatgeat algorithm" has been known. The "Grnatgeat algorithm" realizes an exact three-dimensional reconstruction, on condition that an object has boundaries in the body-axis direction and does not run over a detector (that is, the object is an isolated substance and the detector is able to always detect projection data of all the object; in technical terms, the case is a "Short-object problem with no detector truncation") and the orbit of a focal point satisfies Tuy's data requisite sufficient condition (that is, the condition that all the planes crossing or being tangent to a support of an object cross or are tangent to the orbit of the focal point at least one time). If a circular orbit is employed, the "Grnatgeat algorithm" provides an approximate solution, like the foregoing "Feldkamp+FS."

The three-dimensional reconstruction based on the "Grnatgeat algorithm" is carried out through the following steps 1 to 9.

First, projection data p(β,γ,α) acquired at a focal point p is weighted with cos γ cos α to obtain $G^{(1)}(β,γ,α)$ (step 1).

Then, values $G^{(1)}(β,γ,α)$ on a plane Q(ξ,φ,s) including the focal point β are subjected to area integral (line integral along a straight line L on the detector plane), so that weighted area integral data $G^{(2)}(ξ,φ,s)$ is obtained (step 2).

Then, an area integral data on a plane Q' (straight line L) near the plane Q is used to compute a differential of $G^{(1)}(ξ,φ,s)$, thus a primary differential data $P^{(2)}(ξ,φ,s)$ for three-dimensional Radon data being provided (step 3).

The primary differential data obtained at step 3 is then transformed to the three-dimensional Radon space (rebinning) (step 4).

The foregoing steps 1 to 4 are applied to each of all the focal point positions β (step 5).

Then a redundancy of the three-dimensional Radon data in the three-dimensional Radon space is divided by a reciprocal number of the number of times M(ξ,φ,s) of acquisition of the Radon data, so that the redundancy is corrected (normalized) (step 6). M indicates the number of intersections between the planes and the orbit of the focal point.

The primary differential data is then made to have further differential in the radius direction so as to obtain a secondary differential data $P^{(2)}(ξ,φ,s)$ (step 7).

Further, the secondary differential data $P^{(2)}(ξ,φ,s)$ is subjected to three-dimensional inverse projection onto the plane Q(ξ,φ,s) (step 8).

The computation at the foregoing steps 6 to 8 is applied in a repetitive manner to all necessary data in the three-dimensional Radon space, resulting in the reconstruction of an image of the object f (step 9).

There is another three-dimensional reconstruction algorithm, which is another one from the foregoing "Grnatgeat algorithm." Practically, the rebinning (step 4) is avoided to independently handle data acquired at each focal point. This algorithm has been known as "shift-variant FBP (filtered backprojection) algorithm."

This "shift-variant FBP algorithm" is converted to the "Feldkamp+FS," as long as the foregoing conditions for "Grnatgeat algorithm" (including Tuy's data requisite sufficient condition) are satisfied and a circular orbit is set. (For example, refer to "H. Kudo and T. Saito: "Derivation and implementation of a cone-beam reconstruction algorithm for nonplanar orbits," IEEE Trans. Med. Imag., MI-13, pp.186–195, 1994," and "M. Defrise and R. Clack: "A cone-beam reconstruction algorithm using shift-variant filtering and cone-beam backprojection," IEEE Trans. Med. Imag., MI-13, pp.186–195, 1994.")

Figure 28A:
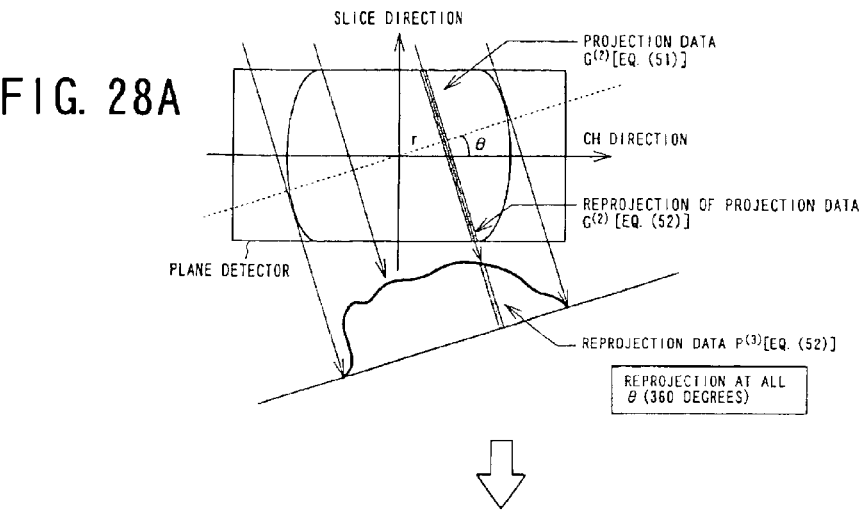
FIGS. 28A to 28C explain a shift-variant FBP algorithm.
Figure 28B:
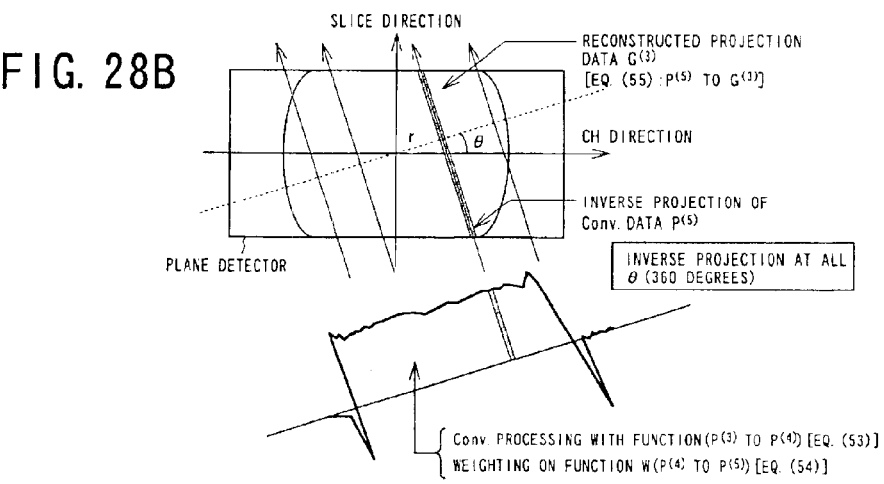
Figure 28C:
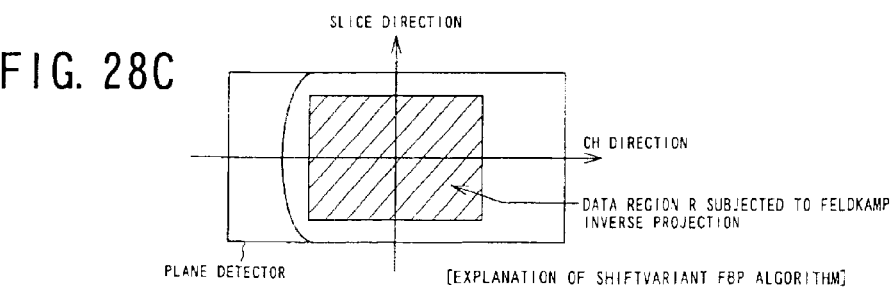

FIGS. 28A to 28C outlines the "shift-variant FBP algorithm." FIG. 28A shows steps (steps 1 and 2), in which projection data acquired by a cone-beam projection from a focal point onto an area detector is used to obtain reprojection data; FIG. 28B shows steps (steps 3 to 9), in which the reprojection data is used to obtain reconstructed data based on the cone-beam inverse projection; and FIG. 28C depicts an example of range of data to be inverse-projected on the area detector using the Feldkamp algorithm, respectively.

This "shift-variant FBP algorithm" is carried out through the following steps 1 to 9.

First, as shown in FIG. 28A, projection data p(β,u,v) acquired at a focal point β is weighted with cos γ cos α to obtain $G^{(2)}(β,u,v)$ (step 1).

Then, values $G^{(2)}(β,u,v)$ on a plane Q(ξ,φ,s) including the focal point are subjected to area integral (line integral along a straight line L on the detector plane), so that weighted area integral data $P^{(3)}(ξ,φ,s)$ as reprojection data is obtained (step 2).

Then, as shown in FIG. 28B, an area integral data on a plane Q'(straight line L) near the plane Q is used to filter the $P^{(3)}(ξ,φ,s,)$ (i.e., differential), thus a primary differential data $p^{(4)}(ξ,φ,S)$ for three-dimensional Radon data being provided (step 3).

Further, by multiplying this $p^{(4)}(ξ,φ,s)$ by a weighting function w, a data redundancy is corrected to obtain $P^{(1)}(ξ,φ,s)$ (step 4). This primary differential $P^{(5)}((ξ,φ,s)$ is subjected to a parallel inverse projection (two-dimensionally) onto the detector plane along the straight line L (step 5).

The foregoing steps 2 to 5 are applied to each of all the angles on the detector plane, so that $G^{(3)}(β,u,v)$ is obtained (step 6). This $G^{(3)}(β,u,v)$ is subject to differential computation in a tangent direction to the moving trajectory of a focal point, that is, in a moving direction of the focal point, resulting in that $G^{(4)}(β,u,v)$ is obtained (step 7). Further, this $G^{(4)}(β,u,v)$ is weighted with use of $L^{-2}$, thus realizing (three-dimensional) cone-beam inverse projection (step 8).

The computation at the foregoing steps 1 to 8 is applied to all the focal point positions β, which allows an image of the object f to be reconstructed (step 9).

The above algorithm can be expressed by following equations (51) to (57):

$$G^{(2)}_β(u, v) = p_β(u, v) \cdot \cos γ \cdot \cos α, \qquad \text{Eq. (51)}$$

$$P^{(3)}_β(r, θ) = \int_{-R_λ}^{R_λ} \int_{-R_λ}^{R_λ} G^{(2)}_β(u, v) \cdot δ(r - u \cdot \cos θ - v \cdot \sin θ) du dv, \qquad \text{Eq. (52)}$$

$$P^{(4)}_β(r, θ) = \int_{-R_λ}^{R_λ} H(r - r') P^{(3)}_β(r', θ) dr', \qquad \text{Eq. (53)}$$

$$P^{(5)}_β(r, θ) = P^{(4)}_β(r, θ) \cdot W_β(r, θ), \qquad \text{Eq. (54)}$$

$$G^{(3)}_β(u, v) = \int_{-π/2}^{π/2} P^{(5)}_β(u \cdot \cos θ + v \cdot \sin θ, θ) d θ, \qquad \text{Eq. (55)}$$

$$G^{(4)}_β(u, v) = \int_{-∞}^{∞} H(u - u') G^{(3)}_β(u', v) du', \qquad \text{Eq. (56)}$$

$$f(x, y, z) = \frac{1}{4π^2} \int_0^{2π} \frac{R}{L^2(β, x, y)} \cdot G^{(4)}_β(u, v) dβ. \qquad \text{Eq. (57)}$$

The function W is called redundancy weighting function and corresponds to a reciprocal number of the number M of intersections of the plane corresponding to both the straight lines on the detector plane and the trajectory of a focal point. This function W may be formed to involve the number M of intersections which are smoothed. In the above example, the explanation has been given on condition that the detector is composed of an area type of detector, but as described above, the detector may be formed by a cylindrical type of detector.

Further, when the foregoing "shift-variant FBP algorithm" is used by three-dimensional reconstruction applied to a circular-orbit scan, the number of intersections between the planes and the orbit along which a focal point is moved is always two. Hence if the equation of $$W_\beta(r,\theta)=\tfrac{1}{2} \qquad \text{Eq.(58)}$$

is substituted into the foregoing equation (54), the equations (51) to (57) can be simplified, thus leading to the equation (32) indicative of the Feldkamp reconstruction.

Meanwhile, if the foregoing "shift-variant FBP algorithm" is applied to a scanning orbit formed of a circle and a straight line, an algorithm that meets the following conditions 1 to 3 can be adopted.

1) As to data existing on planes intersecting only the circular orbit, the number of intersections between the planes and the orbit is always two. Thus, like the above, substituting the equation (54) into the equation (58) will reduce the equations (51) to (57) to the equation (32) indicative of the Feldkamp reconstruction (i.e., condition 1).

2) As to planes intersecting both of the circular orbit and the straight line orbit, the equation (58) will not be used with the data acquired with the circular orbit and the equation of $$W_\beta(r,\theta)=0. \qquad \text{Eq.(59)}$$

will not be used with the data acquired with the straight-line orbit (i.e., condition 2).

3) As to data existing on planes intersecting only the straight-line orbit (not the circular orbit), a redundancy weighting function $W_\beta(r,\theta)$ is given according to the number of intersections with the straight-line orbit to use the equations (51) to (57) (condition 3).

As understood from the above, both of the redundancy weighting function $W_\beta(r,\theta)$ for the three-dimensional reconstruction and the weighting function $w(\beta,\gamma)$ for the two-dimensional reconstruction achieve the same purpose of "correcting the redundancy of the n-th-dimensional Radon data."

Concerning how to design the above redundancy weighting function $W_\beta(r,\theta)$, further algorithms developed from the "Shift-variant FBP algorithm" are proposed (for example, refer to "H. Kudo and T. Saito: "An extended completeness condition for exact cone-beam reconstruction and its application," Conf. Rec. 1994 IEEE Med. Imag. Conf. (Norfolk, Va.) (New York: IEEE) 1710–14," and "H. Kudo and T. Saito: "Fast and stable cone-beam filtered backprojection method for non-planar orbits," 1998 Phys. Med. Biol. 43, pp. 747–760, 1998"). These references teach that the redundancy weighting function $W_\beta(r,\theta)$ is designed to be consistent with either the following purpose 1 or 2.

1) In terms of the technical term, a long-object problem is resolved. This problem arises, for example, in scanning part of the human body. When a detector of which detection width is narrow in the body-axis direction is arranged to the object that is long in the body-axis direction, there may be the problem that the object runs over the detection width. In this case, weights applied to the data acquired from planes running over the detection width are set to zero (purpose 1).

2) An error in computing a reconstruction algorithm can be minimized. If data is associated with a focal point to which horizontal-direction ramp filtering with smaller errors on the same plane is applied and a further focal point to which shift-variant filtering with larger errors is applied, the function M will not be handled equally. In such a case, the data toward the ramp filtering is processed with greater weights, while the data toward the shift-variant filtering processed with lower weights (purpose 2).

Furthermore, as an accurate three-dimensional reconstruction algorithm for a helical scan, a technique called "n-PI method" has also been proposed (refer to "R. Proksa et. al.: "The n-pi-method for helical cone-beam CT," IEEE Trans. Med. Imag., 19, 848–863(2000)). This technique requires three-dimensional Radon data at odd times, such as 1, 3, 5, 7, . . . times, respectively, though other three-dimensional reconstruction algorithms for the helical scan are avoided from redundantly acquiring three-dimensional Radon data. Thus, redundantly acquired data are corrected with the use of the redundancy weighting function $W_\beta(r,\theta)$ (which corresponds an equation (24) described in the reference written by Proksa et al., that is, a function of $$\sum_{i=1}^{\min(n,n_0)} \tilde{M}(l, \bar{\xi}, \lambda_i) = 1$$

corresponds to the redundancy weighting function).

In consequence, the above review for the two-dimensional and three-dimensional reconstruction algorithms reveals explicitly that the conventional setting techniques of the redundancy weighting function W for an accurate three-dimensional reconstruction do no take a factor of "acquisition time" into consideration. That is, such conventional setting techniques do not pay attention to a premise that "an object may move." However, in cases where the three-dimensional reconstruction algorithm is applied to medical CT, a patient (i.e., the object) may move during a scan. Therefore, if ignoring such motion, artifacts surely appear on reconstructed images. Concurrently, it has been desired that temporal resolution be improved.

(3) Principle of three-dimensional reconstruction algorithm according to the present invention The present invention has been made to provide a three-dimensional reconstruction algorithm capable of achieving an object of "removing artifacts caused due to patient's (object's) motion and improving temporal resolution."

In order to achieve the object, the present invention provides the foregoing accurate three-dimensional reconstruction algorithm, in which a redundancy weighting function W is designed based on reliably derived from data acquisition time and three-dimensional Radon data is corrected using the designed redundancy weighting function W.

The redundancy weighting function W designed in the present invention is applicable, without any modification, to any reconstruction algorithm involving a scan that acquires data redundantly (in other words, the same three-dimensional Radon data can be acquired a plurality of times. Furthermore, as will be described later, if it is preferable that a contribution rate of lower-reliability data to images is reduced positively, the correction based on the redundancy weighting function W according to the present invention is applicable to the reconstruction with no redundancy in data acquisition.

The correction that uses the redundancy weighting function W is carried out by the correcting unit 34, every three-dimensional Radon data, that is, every plane Q to be subjected to computation (i.e., area integral) of each three-dimensional Radon data.

The design manual of a redundancy weighting function $W_\beta(r,\theta)$ to be introduced hereafter is based on by the following rules 1 to 3.

First of all, a three-dimensional Radon data acquired at a data acquisition time (or an acquisition time range) with a greater reliability (i.e., a data reliability function T(β) is higher) is, data by data, given a larger weight (rule 1). This rule can be expressed as follows.

$$W_\beta(r,\theta) \to \text{large when } T(\beta) \to \text{large.} \quad \text{Eq.(101)}$$

On the other hand, three-dimensional Radon data acquired at a data acquisition time (or an acquisition time range) with a smaller reliability (i.e., a data reliability function T(β) is lower) is, data by data, given a lower weight (rule 1). This rule can be expressed as follows.

$$W_\beta(r,\theta) \to \text{small when } T(\beta) \to \text{small.} \quad \text{Eq.(102)}$$

The rules 1 and 2 will now be explained more practically.

One scan can be exemplified, as described before, in which the focal point β of the X-ray tube 10 is moved to depict a circular scan (full scan). In this case, a plane Q is assumed (refer to FIG. 20), the plane Q including both the focal point β and a straight line L on the detector plane of the X-ray detector 11 (namely, a plane subjected to computation (area integral) of each three-dimensional Radon data). Though the explanation becomes redundant, the intersections of the circular orbit and the plane Q are explained such that, as long as the plane Q is not completely parallel to a plane formed by the circular orbit, the circular orbit intersects the plane Q at different two positions thereon at different two data acquisition times. Computing an area integral over the plane Q gives Radon data at a point A (refer to FIG. 21). Thus, the intersections at two positions show that the Radon data at the point A is acquired twice.

Figure 33A:
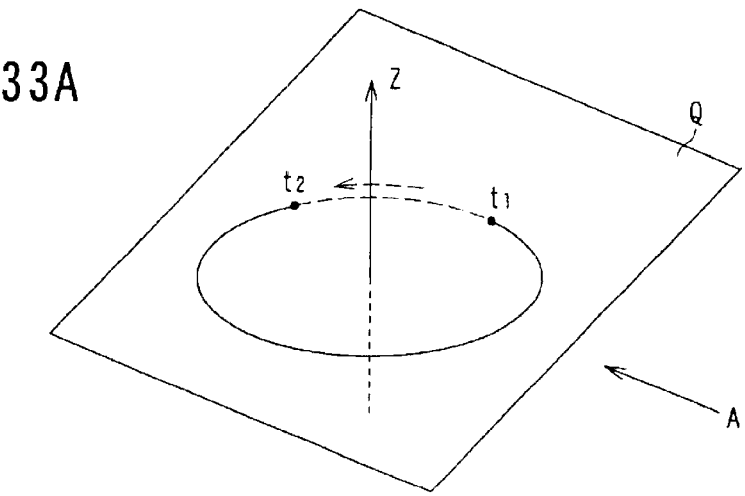
FIGS. 33A and 33B are explanations of redundancy in data acquisition, respectively.
Figure 33B:
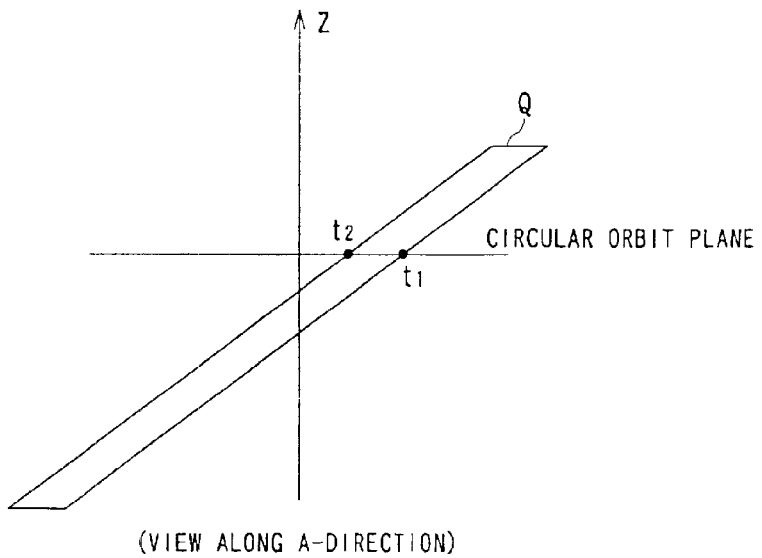
Figure 34A:
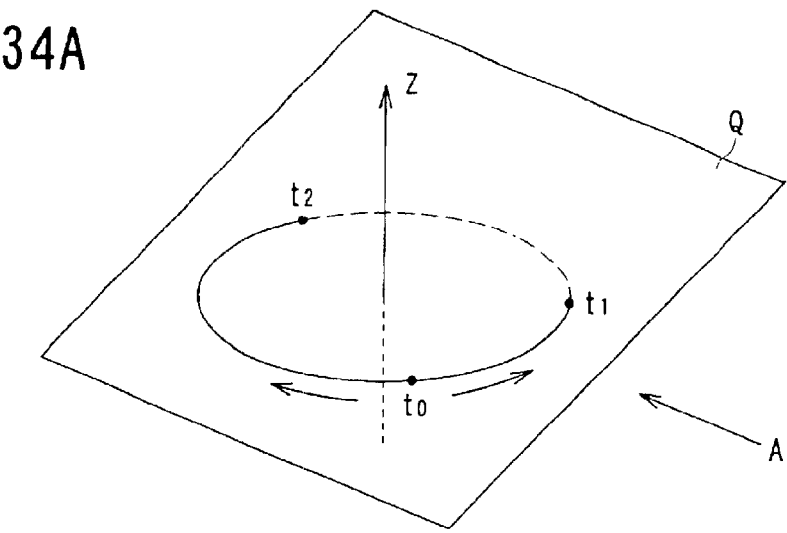
FIGS. 34A and 34B are other explanations of redundancy in data acquisition, respectively.
Figure 34B:
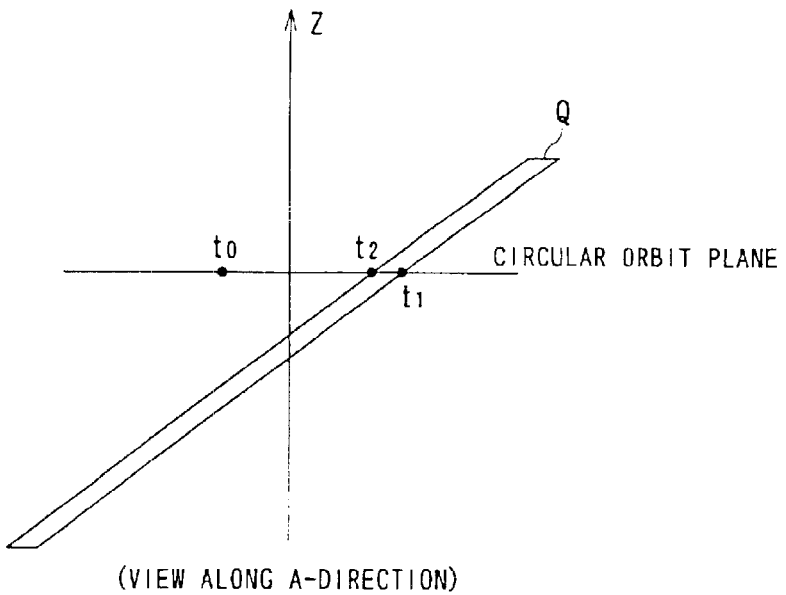

The intersections between the plane Q and the circular orbit plane can be illustrated in plain figures as shown in FIGS. 33A, 33B to 34A, 34B. FIGS. 33B and 34B are drawn, respectively, to pictorially show side views of the FIGS. 33A and 34A, which are observed along a lateral arrow direction "A" depicted thereon.

For example, there are depicted data acquisition times t1 and t2 in FIGS. 33A and 33B. An assumption can be made such that, in order to correct the redundancy of data acquisition, one data acquisition time t1 is assigned to a time instant at which an image is desired and the three-dimensional Radon data is desired to be reconstructed on the basis of this time instant t1. In such a case, the projection data acquired at the remaining time t2 is supposed to be lower in reliability than the one time t1, because there is a possibility that an object to be examined may move during an interval of time from t1 to t2. Thus, the Radon data computed from projection data acquired at the time t1 is given a maximum reliability, while that at the time t2 is given a lower reliability (i.e., lower weight) than that at the time t1. In addition, for example, the larger the difference between the times t1 and t2, the lower the weight at the time t2.

In the case of data acquisition times t1 and t2 shown in FIGS. 34A and 34B, an assumption can be made such that, to correct data acquisition, an middle time to between both times t1 and t2 is a time instant at which an image is desired and the three-dimensional Radon data is desired to be reconstructed on the basis of this time instant to. In such a case, depending on a difference between one interval of time from t0 to t1 and the other interval of time from t0 to t2 (for instance, as the difference becomes large), a lower reliability, i.e., a lower weight is given to acquired data.

Figure 35A:
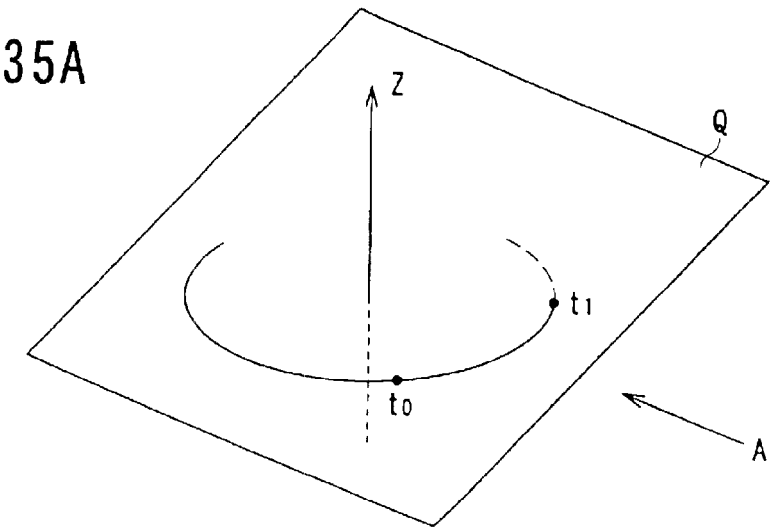
FIGS. 35A and 35B are explanations of data acquisition with no redundancy.
Figure 35B:
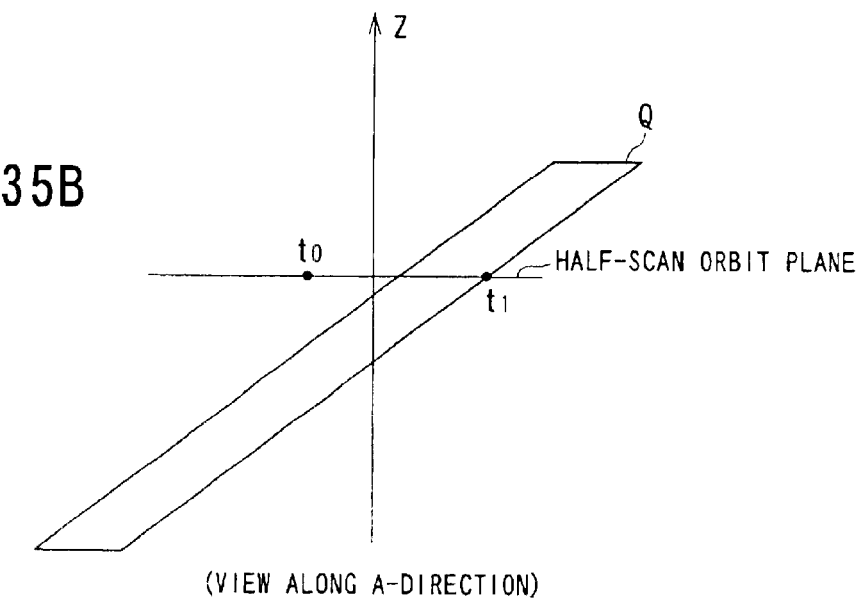
Figure 36:
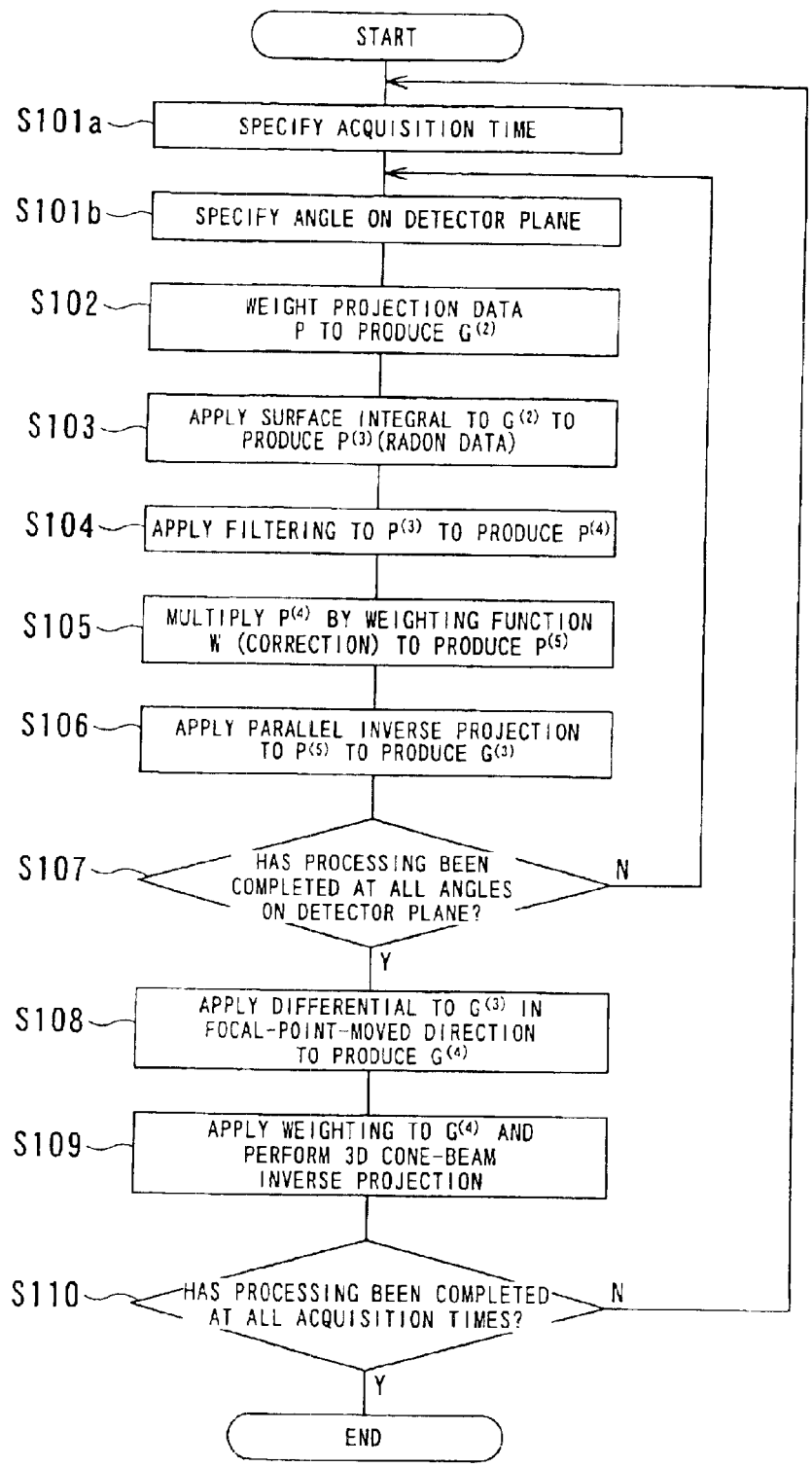
FIG. 36 is a flowchart outlining an example of a three-dimensional reconstruction algorithm to which the present invention is applied.

Further, when a scan requires that the focal point of the X-ray tube 10 be moved to depict a circular orbit (half scan), it can be said from a data-acquisition viewpoint that the orbit of the focal point β intersects the plane Q at only one point, except for the two intersections made in a limited data acquisition range. This is conceptually shown in FIGS. 35A and 35B. FIG. 35B pictorially shows a side view of the FIG. 35A along a lateral arrow "A" shown thereon. In this one-intersection configuration, there is no redundancy in the data acquisition. A time t1 indicates a data acquisition time instant at the solely intersected point. An assumption is made such that, to perform the correction with consideration of reliability of data acquisition, a time to is decided to be a time instant at which an image is desired and three-dimensional Radon data is desired to be reconstructed based on the time to. Thus, according to an absolute time difference between the times t0 to t1 (by way of example, as the time difference becomes larger), a lower reliability (i.e., lower weight) is given to acquired data.

In practice, as will be explained later, reliability functions T corresponding to data acquisition times, which depends on how to scan (i.e., moving trajectories of the X-ray focal point β), are decided in advance, and the reliability functions T are used to compute or decide weights in the form of a redundancy weighting function W.

The remaining rule is that an integral value of weights corresponding to the same plane Q is zero or more and 1 or less and the weights are decided through performing integration on a data reliability function (rule 3). This can be expressed as follows:

$$W^{total}(\xi, \varphi, s) = \sum_{i=1}^{M_\beta(\beta,r,\theta)} W_{\beta_i}(r_i, \theta_i) \quad \text{Eq. (103)}$$

$$= \text{Max}\left[0, \text{Min}\left[\sum_{i=1}^{M_\beta(\beta,r,\theta)} T(\beta_i), 1\right]\right]$$

Accordingly, assuming that the X-ray focal point β depicts a circular orbit, a data reliability function T(β) depending on the circular orbit is decided based on, for example, the following equations (104) and (105):

$$T(\beta) = 3x^2(\beta) - 2x^3(\beta), \quad \text{Eq.(104)}$$

$$x(\beta) = \begin{cases} \dfrac{\beta}{\pi} & 0 \le \beta \le \pi \\ \dfrac{2\pi - \beta}{\pi} & \pi \le \beta \le 2\pi \end{cases} \quad \text{Eq. (105)}$$

Practically using the foregoing rules 1 and 2, these equations can be expressed by the following equation (106):

$$W_\beta(r, \theta) = \begin{cases} \dfrac{T(\beta)}{\sum\limits_{i=1}^{M_\beta(\beta,r,\theta)} T(\beta_i)} & \text{if } \sum\limits_{i=1}^{M_\beta(\beta,r,\theta)} T(\beta_i) \ge 1 \\ T(\beta) & \text{otherwise} \end{cases} \quad \text{Eq. (106)}$$

(Examples of Data Reliability Functions)

Figure 30:
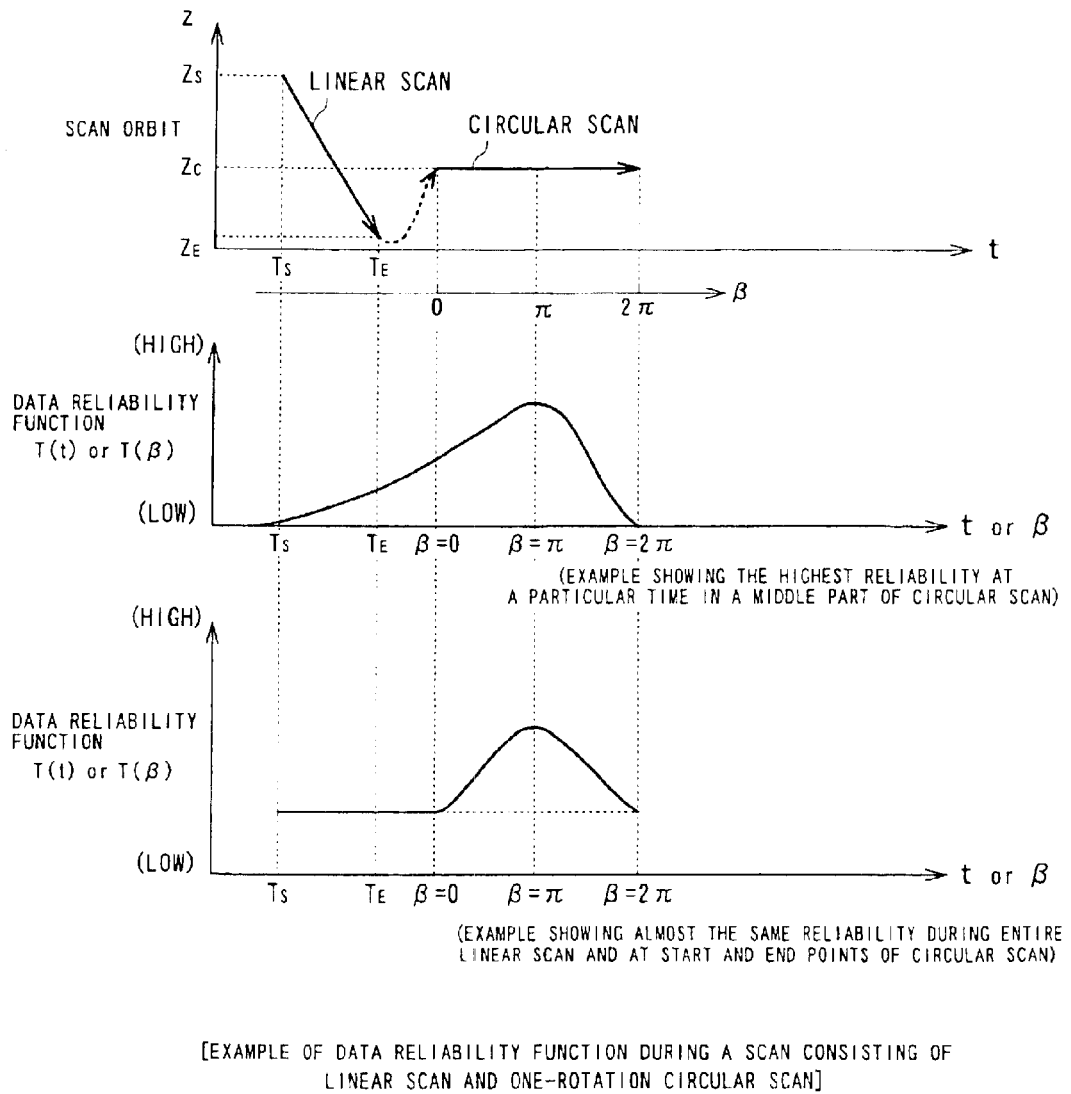
FIG. 30 exemplifies reliability functions of data obtained by a scan consisting of a linear scan and a one-rotation scan.
Figure 31:
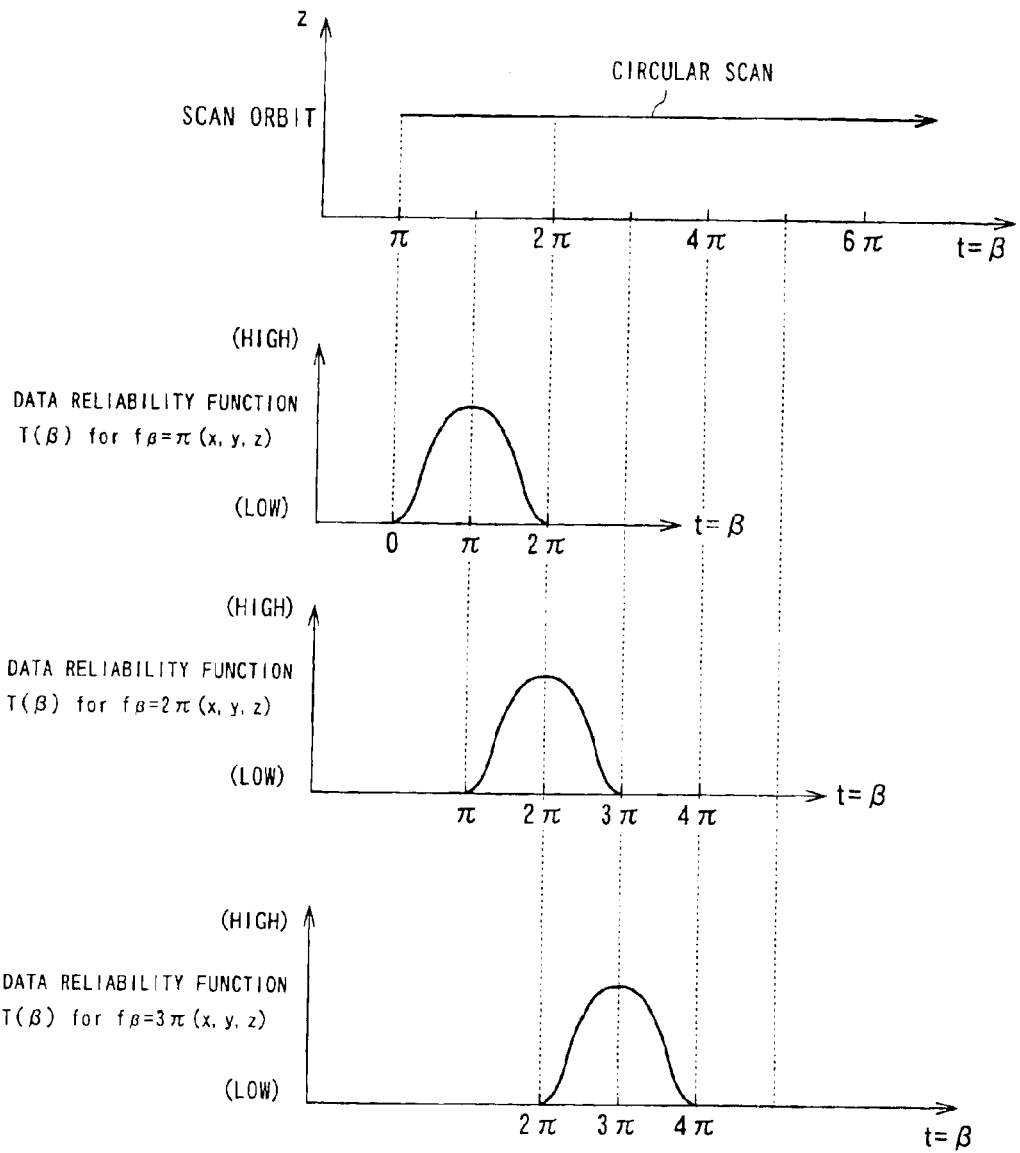
FIG. 31 exemplifies reliability functions of data obtained by a scan consisting of a plurality of continuous rotation scans along a circular orbit.
Figure 32:
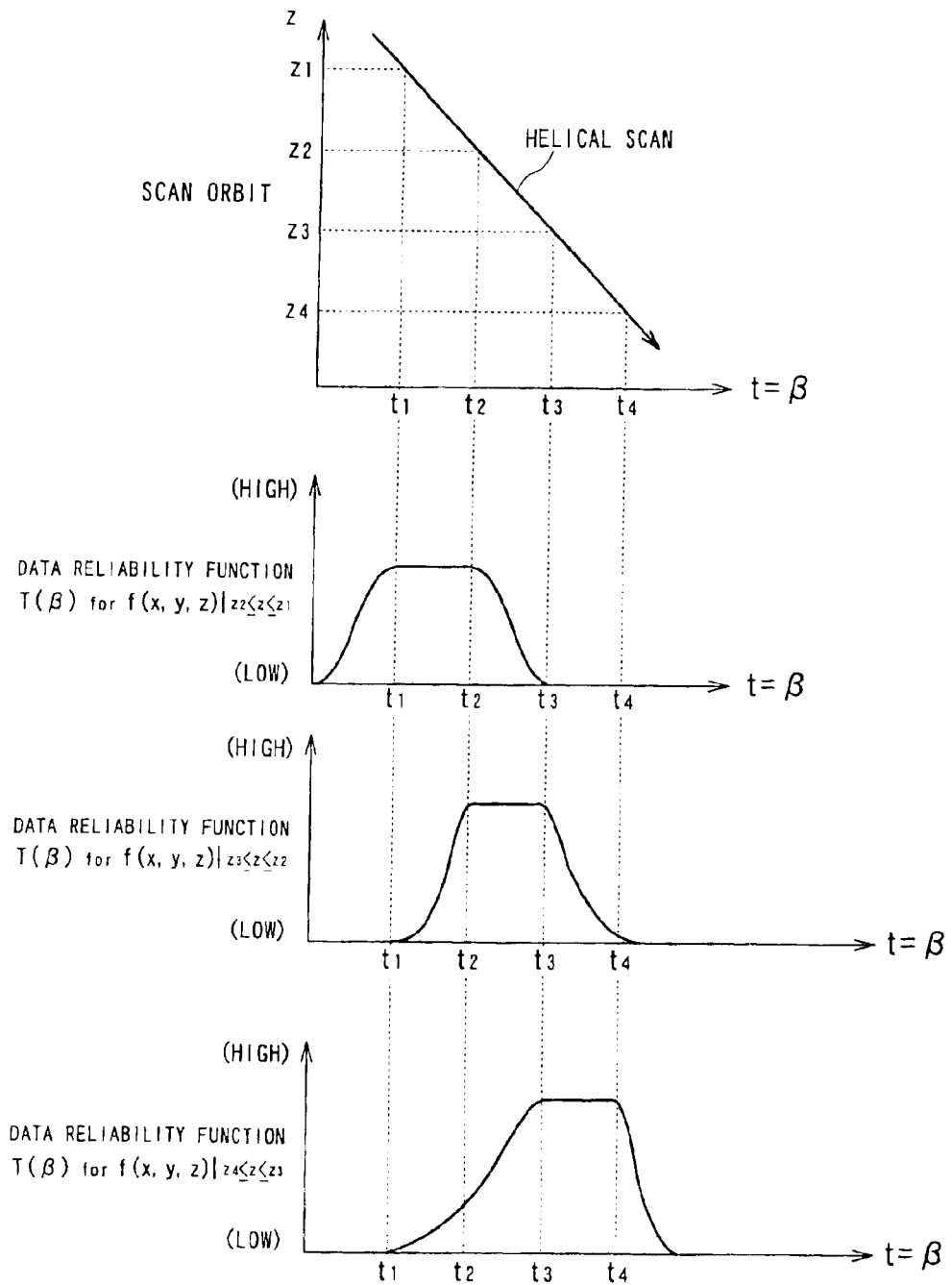
FIG. 32 exemplifies reliability functions of data obtained by a helical scan.

Reliability functions of data according to the present embodiment are set suitably in compliance with scan modes (such as circular scan, linear scan, helical scan and others). FIGS. 30 to 32 exemplify such examples.

FIG. 30 shows a data reliability function $T(\beta)$ or $T(t)$ acquired by a scan mode consisting of a linear orbit and a one-rotation circular orbit. The scan orbit in this example is shown by an upper graph in FIG. 30 (where the longitudinal axis denotes a scan orbit Z and the lateral axis denotes $t=\beta$). As shown therein, the scan orbit Z is made up of a linear scan carried out along the linear direction (i.e., Z-axis direction, rotation-axis direction, or slice direction) during a predetermined section ($Z=Z_S$ to $Z_E$, $t=t_S$ to $t_E$) and a circular scan, which follows the linear scan, carried out at a given position in the linear direction ($Z=Z_C$) by rotating one time along a circumferential direction ($\beta=0$ to $2\pi$).

The reliability function $T(t)$ or $T(\beta)$ for the data acquired along this scan orbit is set such that, as shown at a middle graph in FIG. 30 (where the longitudinal axis denotes $T(t)$ or $T(\beta)$ and the lateral axis denoted t or $\beta$), the center ($\beta=\pi$) in the circular orbit is the highest in reliability. In addition, the reliability function $T(t)$ or $T(\beta)$ is also patterned so as to be the lowest at the scan start/end positions (that is, the start position $Z_C(t=t_S)$ of the linear scan and the end position of the circular scan ($\beta=2\pi$)), while the reliability function $T(t)$ or $T(\beta)$ continuously increases little by little from the start position $Z_C$ of the linear scan, its end position $Z_E(t=t_E)$, the start position (t=0) of the circular scan, to its center ($\beta=\pi$) showing the highest reliability (peak), and then gradually decreases toward the end position ($\beta=2\pi$) of the circular scan.

Another pattern of the reliability function $T(t)$ or $T(\beta)$ directed to the above scan orbit is exemplified by a lower graph in FIG. 30 (wherein the longitudinal axis: $T(t)$ or $T(\beta)$ and the lateral axis: t or $\beta$). Like the above, the reliability function $T(t)$ or $T(\beta)$ is set to its highest value at the center ($\beta=\pi$) of the circular scan, whereas its entire pattern is decided such that the entire of the linear scan and the start/end positions of the circular scan are almost the same low level in reliability, but constant.

In cases where the scan mode consists of a liner scan and a one-rotation circular scan, the examples of the reliability function shown in FIG. 30 are able to establish a three-dimensional reconstruction algorithm more suitable to the cone-beam CT. Hence, the foregoing advantage is given to the reconstruction at the maximum, whereby artifacts due to object's motion can be reduced surely.

Some modifications from the examples in FIG. 30 can be provided. Instead of the above scan mode where the linear scan is followed by the one-rotation circular scan, anther scan mode may be set, where a one-rotation circular scan is first carried out, and then a one-time linear scan is carried out. The reliability function in such a scan mode may be set by reversing in time the graph shown at the middle or lower graph in FIG. 30.

The foregoing scan of which orbit is formed by combining both a linear orbit and a circular orbit with each other may be repeated a plurality of times.

FIG. 31 exemplifies how to determine a data reliability function $T(\beta)$ or $T(t)$, when the scan mode is set to a circular-orbit scan carried out continuously a plurality of times.

In this example, as shown by an uppermost graph in FIG. 31 (where the longitudinal axis: scan orbit Z and the lateral axis: time $t=\beta$), the scan orbit is made by circular scans continuously rotated a plurality of times along a circumferential direction of the orbit located at a given position in the straight-line direction (X=0 to $2\pi$, to $4\pi$, to $6\pi$). The reliability function $T(\beta)$ or $T(t)$ for this can orbit can be exemplified by each graph shown at the second field to the fourth field (lowermost one) in FIG. 31 (where the longitudinal axis: $T(\beta)$ or $T(t)$ and the lateral axis: time $t=\beta$). In each circular scan, the reliability function $T(\beta)$ or $T(t)$ is decided to have the highest value at its center (in this example, $\beta=\pi$ during an interval of $\beta=0$ to $2\pi$, $\beta=2\pi$ during an interval of $\beta=\pi$ to $3\pi$, and $\alpha=3\pi$ during an interval of $\alpha=2\pi$ to $4\pi$).

In cases where the scan mode consists of a circular-orbit scan continuously repeated a plurality of times, the example of the reliability function shown in FIG. 31 is able to establish a three-dimensional reconstruction algorithm more suitable to the cone-beam CT. Hence, the foregoing advantage is given to the reconstruction at the maximum, whereby artifacts due to object's motion can be reduced surely.

FIG. 32 exemplifies a data reliability function $T(\beta)$ or $T(t)$, when the scan mode is set to a helical scan.

In this example, as shown by an uppermost graph in FIG. 32 (where the longitudinal axis: scan orbit Z and the lateral axis: time $t=\beta$), the scan orbit is made by circular scans continuously rotated a plurality of times respectively at different positions in the straight-line direction (Z=Z1 to Z2 to Z3 to Z4, t=t1 to t2 to t3 to t4). The reliability function $T(\beta)$ or $T(t)$ for this can orbit can be exemplified by each graph shown at the second field to the fourth field (lowermost one) in FIG. 32 (where the longitudinal axis: $T(\beta)$ or $T(t)$ and the lateral axis: time $t=\beta$). In each section of the entire helical scan, the reliability function $T(\beta)$ or $T(t)$ is patterned to have the highest and constant value over its central region (in this example, t=t1 to t2 during an interval of below t=t3, t=t2 to t3 during an interval of t=t1 to t4, and t=t3 to t4 during an interval of over t=t4), thus forming an almost trapezoidal pattern.

In cases where the scan mode consists of a helical scan, the example of the reliability function shown in FIG. 32 is able to establish a three-dimensional reconstruction algorithm more suitable to the cone-beam CT. Hence, the foregoing advantage is given to the reconstruction at the maximum, whereby artifacts due to object's motion can be reduced surely.

In the present embodiment, the foregoing reliability function T is applied to, for example, the equation (106) to figure out a redundancy weighting function W. The weights in accordance with the weighting function W is computed by the correcting unit 34 or reconstruction unit 36. The computation on the equation (106) and others may be done every time when the correcting computation is carried out. Alternatively, the weights may be stored beforehand as a memory table in an internal memory of the correcting unit 34 or the data storing unit 35, so that the memory table can be referred to decide weights for the correction.

The procedures for setting the weights can be outlined as follows. First, both of a desired scan orbit (a circular orbit, a combined orbit of linear and circular obits, or others) and a time instant for an image (i.e., image to be reconstructed) are specified. Then, every plane Q, acquisition times (i.e., views) at each of which the scan orbit intersects the plane Q. The views to be acquired is therefore decided every plane Q.

Conversely, pluralities of planes Q to be subjected to acquisition at each view are decided. As a result, as for each plane Q, data acquired from the view Q by another view can be known. Then the temporal relationship between the acquisition times at intersections and the time for a desired image is applied to a reliability function to decide data reliability. The reliability thus-decided is then applied to a redundancy weighting function to decide weights depending on the reliability. This makes it possible that, by way of example, data acquired at time instants near to the time instant for the desired image are given larger weighs, while data acquired at time instants far from the time for the desired image are given relatively smaller weights.

The above setting may be executed in parallel with or beforehand the three-dimensional reconstruction processing.

Processing for image reconstruction based on an actual three-dimensional reconstruction algorithm will now be described, in which a redundancy weighting function W obtainable based on the foregoing design guidelines is used.

(Shift-variant FBP Algorithm (Part 1))

An application example to the Shift-variant FBP algorithm serving as a three-dimensional reconstruction algorithm will now be explained. The processing for this algorithm is conducted cooperatively by both the correcting unit 34 and the reconstruction unit 36 according to the procedures of steps S101a to S10 shown in FIG. 36 in this order.

A given acquisition time is first specified (step S101a), and then a given angle on a detector plane is specified (step S101b). Projection data p(β,u,v) acquired in consistency with the position of this focal point β and the angular position on the detector plane (that is, a plane to be subjected to integration) is then weighted by using cos γ cos α to obtain $G^{(2)}(\beta,u,v)$ (step S102).

The values $G^{(2)}(\beta,u,v)$ existing on the plane Q(ξ,φ,s) including the focal point are then applied to area integral (on the detector plane, line integral along the straight line L), so that a weighted area-integral data $P^{(3)}(\xi,\phi,s)$ (step S103).

Using data from a plane Q' (straight line L1) near to the plane Q, the $P^{(3)}(\xi,\phi,s)$ is filtered (differentiated) to obtain the primary differential data $P^{(4)}(\xi,\phi,s)$ for the three-dimensional Radon data (step S104).

Then, the data $P^{(4)}(\xi,\phi,s)$ is multiplied by a weighting function $W_\beta(r,\theta)$ based on a reliability function T(β) obtained from the foregoing equations (101) to (106), so that its redundancy is corrected to produce $P^{(5)}(\xi,\phi,s)$ (step S105).

The primary differential value $P^{(5)}(\xi,\phi,s)$ for the three-dimensional Radon data is inversely projected (two-dimensionally) in parallel to the straight line L onto the detector plane (step S106).

The foregoing steps S101b to S106 are applied to each of all the angles on the detector plane, so that $G^{(3)}(\beta,u,v)$ is obtained (step 107).

This $G^{(3)}(\beta,u,v)$ is subject to differential computation in a tangent direction to the moving trajectory of a focal point, that is, in a moving direction of the focal point, resulting in that $G^{(4)}(\beta,u,v)$ is obtained (step 108).

Further, this $G^{(4)}(\beta,u,v)$ is weighted with use of $L^{-2}$, thus realizing (three-dimensional) cone-beam inverse projection (step 109).

The computation at the foregoing steps 101a to 109 is applied to all the focal point positions β in the data acquisition range, which allows an image of the object f to be reconstructed (step 110).

The above algorithm can be expressed by following equations (111) to (117):

$$G^{(2)}_\beta(u, v) = p_\beta(u, v) \cdot \cos\gamma \cdot \cos\alpha, \qquad \text{Eq. (111)}$$

$$P^{(3)}_\beta(r, \theta) = \int_{-R_\lambda}^{R_\lambda} \int_{-R_\lambda}^{R_\lambda} G^{(2)}_\beta(u, v) \cdot \delta(r - u \cdot \cos\theta - v \cdot \sin\theta) du dv, \qquad \text{Eq. (112)}$$

$$P^{(4)}_\beta(r, \theta) = \int_{-R_\lambda}^{R_\lambda} H(r - r') P^{(3)}_\beta(r', \theta) dr', \qquad \text{Eq. (113)}$$

$$P^{(5)}_\beta(r, \theta) = P^{(4)}_\beta(r, \theta) \cdot W_\beta(r, \theta), \qquad \text{Eq. (114)}$$

$$G^{(3)}_\beta(u, v) = \int_{-\frac{\pi}{2}}^{\frac{\pi}{2}} P^{(5)}_\beta(u \cdot \cos\theta + v \cdot \sin\theta, \theta) d\theta, \qquad \text{Eq. (115)}$$

$$G^{(4)}_\beta(u, v) = \int_{-\infty}^{\infty} H(u - u') G^{(3)}_\beta(u', v) du', \qquad \text{Eq. (116)}$$

$$f(x, y, z) = \frac{1}{4\pi^2} \int_0^{2\pi} \frac{R}{L^2(\beta, x, y)} \cdot G^{(4)}_\beta(u, v) d\beta. \qquad \text{Eq. (117)}$$

In this example, if the reliability function T(β) and/or the redundancy weighting function Wβ(r,θ) are allowed to have negative values, extrapolation can be done. When a reliable region is made to narrow by extending a zero-filling region, temporal resolution can be enhanced further (at the sacrifice of a data acquisition rate).

(Scan Moving Along Orbit Formed by Combining Linear and Circular Orbits of X-ray Focal Point)

In addition, another example in which the foregoing redundancy weighting function W is used will now be described, the function W being applied to a reconstruction algorithm based on a scan formed by mutually combining a straight-line scan and a circle of the X-ray focal point β.

First, the orbit λ(β) of the focal point is defined by the following equations (121) and (122):

$$\lambda(\beta) = \begin{cases} (0, R, \beta + a)^T & \text{if } -2a \leq \beta \leq 0 \\ (-R\sin\beta, R\cos\beta, 0)^T & \text{if } 0 \leq \beta \leq n \cdot 2\pi' \end{cases} \qquad \begin{array}{l}\text{Eq. (121)}\\ \text{Eq. (122)}\end{array}$$

$n$ = integer.

It is assumed that of these, data in a range expressed by the equation (123) is used to reconstruct an image of the object f.

$$\lambda(\beta) = \begin{cases} (0, R, \beta + a)^T & \text{if } -2a \leq \beta \leq 0 \\ (-R\sin\beta, R\cos\beta, 0)^T & \text{if } (2k-1)\cdot\pi - \frac{b}{2} \leq \beta \leq (2k+1)\cdot\pi + \frac{b}{2} \end{cases} \qquad \text{Eq. (123)}$$

In this case, both of a data reliability function $T(\beta)$ and a redundancy weighting function $W\beta(r,\theta)$ are defined by the following equations (124) and (125), respectively:

$$T(\beta) = \frac{1}{2} \times \begin{cases} \frac{2a+\beta}{2a} \cdot e^{-ck} & \text{if } -2a \leq \beta \leq 0 \\ \frac{\beta - (2k-1)\cdot\pi - \frac{b}{2}}{b} & \text{if } (2k-1)\cdot\pi - \frac{b}{2} \leq \beta \leq (2k-1)\cdot\pi + \frac{b}{2} \\ 1 & \text{if } (2k-1)\cdot\pi + \frac{b}{2} \leq \beta \leq (2k+1)\cdot\pi - \frac{b}{2} \\ \frac{(2k+1)\cdot\pi + \frac{b}{2} - \beta}{b} & \text{if } (2k+1)\cdot\pi - \frac{b}{2} \leq \beta \leq (2k+1)\cdot\pi + \frac{b}{2} \end{cases}$$
Eq. (124)

$$W_\beta(r,\theta) = T^2(\beta).$$

$$W_\beta(r,\theta) = \begin{cases} \frac{T(\beta)}{\sum_{i=1}^{M_\beta(\beta,r,\theta)} T(\beta_i)} & \text{if } \sum_{i=1}^{M_\beta(\beta,r,\theta)} T(\beta_i) \geq 1 \\ T(\beta) & \text{otherwise} \end{cases}$$
Eq. (125)

In addition to the above, the three-dimensional reconstruction algorithm according to this example is also applicable to all three-dimensional reconstruction algorithms, such as Grangeat algorithm and n-PI method. Even reconstruction algorithms with no redundancy in data acquisition can use the basic concept that, as sated in the foregoing rules 1 to 3, "weighting for three-dimensional Radon data is decided based on data reliability such that the sum of the weights for the same three-dimensional Radon data becomes a value in a range of 0 to 1," as long as "it is desired to lower weights for data with lower reliability in order to get excellent results, though a data acquisition rate is reduced."

The detector applied to the three-dimensional reconstruction algorithm according to this example can be composed of any type of detector, such as flat area type, cylindrical type, or spherical surface type.

(Shift-variant FBP Algorithm (Part 2))

Another example of the three-dimensional reconstruction algorithm will now be described.

Figure 29:
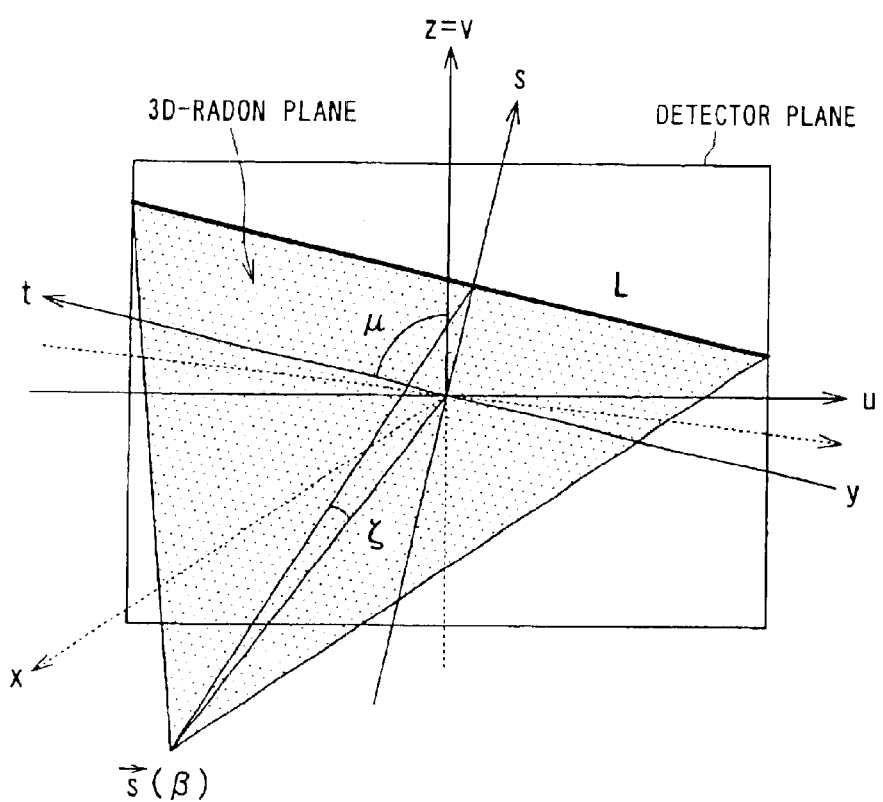
FIG. 29 explains a geometry used for examples based on other three-dimensional reconstruction algorithms.

FIG. 29 explains the geometries of this example. In the geometries on the detector plane shown in FIG. 29, there is shown a cone-beam vertex position $s(\beta)$ (s: vector) of the focal point $\beta$ that project a cone beam toward a point (u,v) on the detector plane, so that projection data $g(u,v,\beta)$ is produced. The $g(u,v,\beta)$ can be computed along a circular orbit based on the following equations (129) and (130):

$$g(u,v,\beta) = \int_0^\infty dl f(\vec{s}(\beta) + l\vec{\alpha}_{u,v,\beta}),$$
Eq. (129)

$$\vec{s}(\beta) = (R\cos\beta, R\sin\beta, 0)^T, \quad 0 \leq \beta \leq 2\pi n$$
Eq.(130)

f(r) denotes an object to be reconstructed (r: vector) and R denotes the radius of the circular orbit, and $\alpha_{u,v,\beta}$ is a unit vector, respectively.

Using the above geometries, the three-dimensional reconstruction algorithm according to this example is processed such that 1): a data reliability function $T(\beta)$ is defined, 2): based on the function $T(\beta)$ for three-dimensional Radon data, a redundancy weighting function $w(s,\mu,\beta)$ is computed, and 3): the function $w(s,\mu,\beta)$ is applied to the Shift-variant FBP algorithm. The processing at each step will now be detailed.

First, as to the data reliability function $T(\beta)$, under the rules of 1): the function $T(\beta-\beta_0)$ decreases with decreasing $|\beta-\beta_0|$ and 2): $\partial T(\beta)/\partial$ has contiguity, the following equations (131) and (132) are defined:

$$T(\beta-\beta_0) = 3x^2(\beta-\beta_0) - 2x^3(\beta-\beta_0),$$
Eq.(131)

$$x(\beta) = 1 - |\beta/\pi|.$$
Eq.(132)

Then, concerning the redundancy weighting function $w(s,\mu,\beta)$, under the rules of 1): the function $w(s,\mu,\beta)$ increases with increasing $T(\beta)$, 2): the sum of weights of the function $w(s,\mu,\beta)$ on the same three-dimensional Radon plane becomes 1, and 3): the function $w(s,\mu,\beta)$ has continuity in the s-$\mu$ coordinate system, the following equations (134) and (135) are defined:

$$W_e(s,\mu,\beta) = T(\beta) \Big/ \sum_{i=1}^{M(\beta,r,\theta)} T(\beta_i);$$
Eq. (133)

$$\beta \in [\beta_0 - \pi, \beta_0 + \pi].$$

$$W(s,\mu,\beta) = W_e(s,\mu,\beta) * \text{smooth}(s,\mu).$$
Eq.(134)

Figure 37:
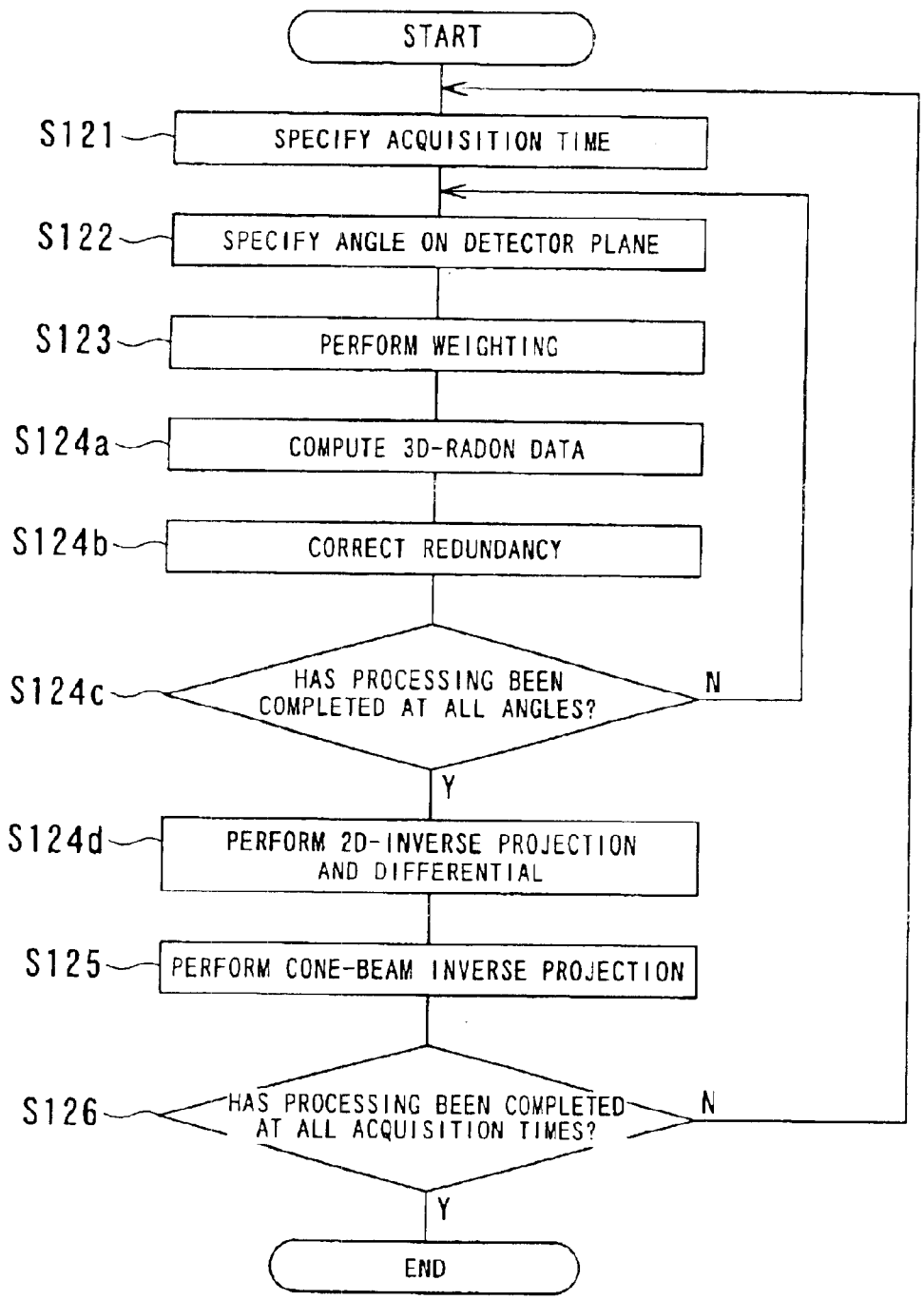
FIG. 37 is a flowchart outlining another example of a three-dimensional reconstruction algorithm to which the present invention is applied.

Then, through the steps S121 to S126 shown in FIG. 37, the redundancy weighting function $w(s,\mu,\beta)$ if obtained as above is applied to the Shift-variant FBP technique, thus reconstructing the object f. The processing at a series of steps shown in FIG. 37 is carried out by both the correcting unit 34 and the reconstruction unit 36 in a cooperative manner.

Briefly, a given acquisition time and a position on the detector plane are specified (steps S121 and S122). Then, using the following equation (135), the weighting is carried out (step S123).

$$\bar{g}(u,v,\beta) = \cos\eta(u,v)\cdot g(u,v,\beta).$$
Eq.(135)

Then the shift-variant filtering is carried out (step S124). This step 2 is composed of the following sub-steps 2a to 2c.

First, using the following equation (136), three-dimensional Radon-data is computed by area integral (sub-step S124a).

$$S(s,\mu,\beta) = \int_{-\infty}^\infty dt \frac{\partial}{\partial s} \bar{g}^\mu(u,v,\beta).$$
Eq. (136)

Then using the following equation (137), data redundancy is corrected (sub-step S124b).

$$S_W(s,\mu,\beta) = W(s,\mu,\beta)\cdot S(s,\mu,\beta).$$
Eq.(137)

The above processing will be repeated respectively for all lines specified on the detector plane (that is, all the planes to be targeted for the area integral) (sub-step S124c).

After this, using the following equation (138), both of two-dimensional projection and differential computation along the axis are carried out.

$$g^F(u, v, \beta) = \frac{\partial}{\partial u} \int_{-\frac{\pi}{2}}^{\frac{\pi}{2}} d\mu \frac{-1}{4\pi^2} S_W(u, v, \beta).$$ Eq. (138)

Cone-beam inverse projection will then follow, so that an image of the object f is reconstructed (step S125). The above processing will be repetitively carried out at all the positions within a necessary data acquisition range of the X-ray focal point β (namely, all the data acquisition times) (step S126).

As described so far, in an X-ray CT scanner constructed above, both of the X-ray tube 10 and the two-dimensional detector 11 are driven to rotate in the R—R technique, during which rotation an X-ray beam is continually projected from the X-ray tube 10 toward an object P, based on a scan method, such as multiple scan or helical scan. The continuously radiated X-ray is formed into a cone beam by the pre-collimator 22, and radiated onto the object P. The X-ray that has transmitted the object P is detected by the two-dimensional detector 11 and its amount is read out as projection data. The read-out projection data is sent to the correcting unit 34 via the data transmission system 28, where the data is subject to various types of correction, before being stored view by view in the data storing unit 35.

The stored data, when read out, is subjected to any algorithm for the foregoing three-dimensional reconstruction (for instance, an algorithm shown by the foregoing steps S101a to S110) carried out by the reconstruction unit 36. This produces a reconstructed image of the object P, which is stored in the data storing unit 36 for preservation and is sent to the display processor 37, under the control of the main controller 30. By the display processor 37, the reconstructed data undergoes necessary processing, such as coloring and superposition of annotation data and scan information, and then is sent to the display 38 where the data is D/A-converted for display in the mode of a tomographic image or volume image (three-dimensional image).

Accordingly, the foregoing fan-beam MHS (two-dimensional circular-orbit modified half scan) has the capability of not only weighting three-dimensional data with the use of the same weights as that obtained on the assumption that an imaginary fan angle 2Γm is set to π but also entitling the focal-point rotation plane (the plane at z=0) to have the similar effect to that given by the MHS (2Γm=π) for the two-dimensional fan-beam algorithm. Concretely, 1): a reasonable data acquisition rate for the three-dimensional Radon data can be obtained based on data reliability, 2): temporary resolution can be upgraded to T/2, 3): precision in a small cone angle can be maintained, and 4): artifacts on images are suppressed remarkably due to continuity in the weights.

In the present embodiment, therefore, for applying the cone-beam-CT three-dimensional reconstruction algorithm to medical CT systems, the artifacts arising on account of object's motion can be lessened and the temporal resolution can be improved.

In the above present embodiment and its applications, the X-ray CT scanner has been described as being a scanner in the third generation, but this is not a definitive list. The reconstruction technique described above is also applicable to CT Scanners in the fourth generation, multi-tube CT scanners for fast scanning (i.e., scanners belonging to the third generation, but are provided with plural pairs of an X-ray tube and a detector), CT scanners in the fifth generation (i.e., no X-ray tube is equipped, while an electronic beam is made to impinge at different positions on a ring-like target so as to rotate the X-ray focal point), and others. In addition, the X-ray detector is not limited to the flat panel type, and other various types of detector, such as cylindrical type, can be adopted as well.

For the sake of completeness, it should be mentioned that the embodiment and various applications explained so far are not definitive lists of possible embodiments. The expert will appreciates that it is possible to combine the various construction details or to supplement or modify them by measures known from the prior art without departing from the basic inventive principle.

What is claimed is:

1. An X-ray CT system comprising:
   an X-ray source for radiating a cone-beam X-ray;
   a two-dimensional X-ray detector for detecting the X-ray radiated from the X-ray source through an object to be examined and for outputting projection data depending on an amount of the detected X-ray;
   scanning means configured to scan the object with the X-ray radiated from the X-ray source within a particular scan range predetermined spatially under a desired scan technique involving at least a movement of the X-ray source along a predetermined orbit for the scan, thus enabling the X-ray detector to acquire the projection data generated during the scan;
   a Radon data producing means for producing three-dimensional Radon data distributed three-dimensionally, from the projection data acquired by the scanning means;
   weighting means for weighting the three-dimensional Radon data using a weighting function providing a non-constant weight in which a degree of reliability of the projection data is reflected, the degree of reliability being previously determined depending on an acquisition time of the projection data during the scan along the orbit; and
   reconstruction means for reconstructing the three-dimensional Radon data weighted by the weighting means, based on a desired three-dimensional reconstruction algorithm, the reconstruction providing an image.

2. The X-ray CT system according to claim 1, wherein the weighting function is set according to a type of the scan technique.

3. The X-ray CT system according to claim 2, wherein the scan technique is one selected from a group of scan techniques including a circular-orbit full scan representing as the orbit a one-time circular orbit, a circular-orbit half scan (MIHS: Modified Half Scan) along an extended circle using the projection data from the scan range of 360 degrees while the orbit representing a one-time circular orbit, a circular-orbit under scan representing as the orbit a one-time circular orbit, a circular-orbit scan representing as the orbit two or more rotations along a circular orbit, a scan representing as the orbit an orbit formed by combining a linear orbit and a circular orbit, and a helical scan representing as the orbit a helical orbit.

4. The X-ray CT system according to claim 3, wherein the scan technique is set to apply to the object, a plurality of times, the scan representing as the orbit an orbit formed by combining a linear orbit and a circular orbit in this order, and
   wherein the weighting unit is configured to weight the three-dimensional Radon data produced from the projection data acquired in the scan range, as to a plurality of times of production of the three-dimensional Radon data performed every predetermined period of time residing in a data acquisition time zone of the plurality of times of scans, every predetermined period of time for each scan, by using the weighting function giving not only a maximum weight at both a data acquisition time representative of a time of the reconstructed image and another data acquisition time falling in a smaller temporal range including the data acquisition time representing the maximum weight but also giving a minimum weight at both data acquisition times at which each predetermined period of time for each scan is started and ended respectively.

5. The X-ray CT system according to claim 3, wherein the scan technique is set to apply to the object the scan representing the two or more rotations along the circular orbit, and wherein the weighting unit is configured to weight, each time of the plurality of times of scans, the three-dimensional Radon data produced from the projection data acquired by using, as the weighting function, a weighting function giving not only a maximum weight at a data acquisition time representative of a time of the reconstructed image but also a smaller weight at another data acquisition time different from the data acquisition time representing the maximum weight.

6. The X-ray CT system according to claim 3, wherein the scan technique is the helical scan technique, and wherein the weighting means is configured to weight, of the three-dimensional Radon data produced on the helical scan technique, the three-dimensional Radon data produced from the projection data acquired by using, as the weighting function, as a weighting function giving not only a maximum and constant weight during a given period of time of which centermost time is representative of a data acquisition time for the three-dimensional Radon data acquired during each data acquisition time zone necessary for reconstructing the image but also a minimum weight at both data acquisition times at which each data acquisition time zone is started and ended respectively.

7. The X-ray CT system according to claim 3, wherein the scan technique is set to apply to the object, one time, a scan representing as the orbit an orbit formed by combining a linear orbit and a circular orbit in this order, and wherein the weighting unit is configured to weight the three-dimensional Radon data produced from the projection data acquired by using, as the weighting function, a weighting function giving not only a maximum weight at both a data acquisition time representative of a time of the image and another data acquisition time falling into a smaller temporal range including the data acquisition time representing the maximum weight but also giving a minimum weight at both of a data acquisition time when the movement along the linear orbit is started and a further data acquisition time when the movement along the circular orbit is ended.

8. The X-ray CT system according to claim 7, wherein the weighting function is formed to maintain the minimum weight at all data acquisition times along the linear orbit.

9. The X-ray CT system according to claim 3, wherein the scan technique is set apply to the object, one time, a scan representing as the orbit an orbit formed by combining a linear orbit and a circular orbit in this order, and wherein the weighting unit is configured to weight the three-dimensional Radon data produced from the projection data acquired by using, as the weighting function, a weighting function giving not only a maximum weight at both a data acquisition time representative of a time of the image reconstructed by the reconstruction means and another data acquisition time falling into a smaller temporal range including the data acquisition time representing the maximum weight but also giving a minimum weight at both of a data acquisition time when the movement along the circular orbit is started and a further data acquisition time when the movement along the circular orbit is ended.

10. The X-ray CT system according to claim 9, wherein the weighting function is formed to maintain the minimum weight at all data acquisition times along the linear orbit.

11. A three-dimensional reconstruction method comprising the steps of:

acquiring two-dimensional projection data into which a three-dimensional distribution of an X-ray absorption coefficient of an object to be examined is reflected, by scanning the object with a cone-beam X-ray;

producing three-dimensional Radon data from the projection data;

correcting the three-dimensional Radon data based on a weighting function in which a degree of reliability of the projection data is reflected, the degree of reliability being previously decided depending on an acquisition time of the projection data; and reconstructing the three-dimensional Radon data based on a three-dimensional reconstruction algorithm to obtain an image of the object.

12. The three-dimensional reconstruction method according to claim 11, wherein the correcting step is configured to correct the three-dimensional Radon data by using the weighting function, correspondingly to each plane to be subjected to surface integral for respectively obtaining the three-dimensional Radon data.

13. The three-dimensional reconstruction method according to claim 12, wherein the degree of reliability of the projection data is composed of a reliability function of the projection data made to relate to each focal point position of the cone-beam X-ray and the weighting function is a redundancy correcting function made to relate to the reliability function of the projection data.

14. The three-dimensional reconstruction method according to claim 13, wherein the reliability function of the projection data is set depending on a scan type of the X-ray.

15. The three-dimensional reconstruction method according to claim 15, wherein the scan technique of the cone-beam X-ray is one selected from a group of scan techniques including a scan technique based on a circular-orbit full scan representing as the orbit a one-time circular orbit, a circular-orbit half scan (MHS: Modified Half Scan) along an extended circle using the projection data from the scan range of 360 degrees while the orbit representing a one-time circular orbit, a circular-orbit under scan representing as the orbit a one-time circular orbit, a circular-orbit scan representing as the orbit two or more rotations along a circular orbit, a scan representing as the orbit an orbit formed by combining a linear orbit and a circular orbit, and a helical scan representing as the orbit a helical orbit.

16. A weight setting method for X-ray CT comprising the steps of:

deciding a degree of reliability for two-dimensional projection data on the basis of a acquisition time of the two-dimensional projection data in which a three-dimensional distribution of an X-ray absorption coefficient of an object to be examined is reflected, the three-dimensional distribution being acquired with a cone-beam X-ray; and deciding a weight used to correct a three-dimensional Radon data obtained from the projection data on the basis of the degree of reliability.

17. The weight setting method for X-ray CT according to claim 16, wherein the step of deciding the degree of reliability includes computing a reliability function of the projection data made to relate to the data acquisition time and the step of deciding the weight includes computing a value of a redundancy correcting function made to relate to the reliability function of the projection data.

18. An X-ray CT system comprising:

an X-ray source configured to radiate a cone-beam X-ray;

a two-dimensional X-ray detector configured to detect the X-ray radiated from the X-ray source through an object to be examined and output projection data depending on an amount of the detected X-ray;

a scanning unit configured to scan the object with the X-ray radiated from the X-ray source within a particular scan range predetermined spatially under a desired scan technique involving at least a movement of the X-ray source along a predetermined orbit for the scan, thus enabling the X-ray detector to acquire the projection data generated during the scan;

a Radon data producing unit configured to produce three-dimensional Radon data distributed three-dimensionally, from the projection data acquired by the scanning unit;

a weighting unit configured to weight the three-dimensional Radon data using a weighting function providing a non-constant weight in which a degree of reliability of the projection data is reflected, the degree of reliability being previously determined depending on an acquisition time of the projection data during the scan along the orbit; and a reconstruction unit configured to reconstruct the three-dimensional Radon data weighted by the weighting unit, based on a desired three-dimensional reconstruction algorithm, the reconstruction providing an image.

19. The X-ray CT system according to claim 18, wherein the scanning unit is configured to move the X-ray source to represent, as the predetermined orbit, an orbit including, as the scan range, a path consisting of at least "180 degrees plus a fan angle of the cone-beam X-ray" around the object.

20. The X-ray CT system according to claim 18, wherein the weighting unit is configured to perform the weighting correspondingly to each plane to be subjected respectively to surface integral for obtaining the three-dimensional Radon data.

21. The X-ray CT system according to claim 20, wherein the weighting unit is configured to weight the three-dimensional Radon data produced from the projection data acquired in the scan range in the scan range by using, as the weighting function, a weighting function giving not only a maximum weight at a data acquisition time representative of a time of the reconstructed image but also a smaller weight at another data acquisition time different from the data acquisition time representing the maximum weight.

22. The X-ray CT system according to claim 20, wherein the weighting unit is configured to weight the three-dimensional Radon data produced from the projection data acquired by using, as the weighting function, a weighting function giving not only a maximum weight at both a data acquisition time representative of a time of the reconstructed image and another data acquisition time falling into a smaller temporal range including the data acquisition time representing the maximum weight but also giving a smaller weight at another data acquisition time different from the data acquisition time representing the maximum weight.

23. The X-ray CT system according to claim 20, further comprising providing means for providing weighting information on the weighting function every plane.

24. The X-ray CT system according to claim 20, wherein the weighting unit is configured to weight the three-dimensional Radon data produced from the projection data acquired by using, as the weighting function, a weighting function giving not only a maximum weight at a data acquisition time representative of a time of the reconstructed image but also a weight becoming smaller as going away from the data acquisition time representing the maximum weight.

25. The X-ray CT system according to claim 24, wherein the scan technique is set to apply to the object, one time, a scan representing as the orbit an orbit formed by combining a circular orbit and a linear orbit in this order, and wherein the weighting unit is configured to weight the three-dimensional Radon data produced from the projection data acquired by using, as the weighting function, a weighting function giving not only a maximum weight at both a data acquisition time representative of a time of the reconstructed image and another data acquisition time falling into a smaller temporal range including the data acquisition time representing the maximum weight but also giving a minimum weight at both of a data acquisition time when the movement along the circular orbit is started and a further data acquisition time when the movement along the linear orbit is ended.

* * * * *